US010500002B2

(12) United States Patent
Simaan et al.

(10) Patent No.: US 10,500,002 B2
(45) Date of Patent: *Dec. 10, 2019

(54) DEXTEROUS WRISTS

(71) Applicant: Vanderbilt University, Nashville, TN (US)

(72) Inventors: Nabil Simaan, Nashville, TN (US); Roger E. Goldman, New York, NY (US); Andrea Bajo, Fort Lauderdale, FL (US)

(73) Assignee: Vanderbilt University, Nashville, TN (US)

( * ) Notice: Subject to any disclaimer, the term of this patent is extended or adjusted under 35 U.S.C. 154(b) by 247 days.

This patent is subject to a terminal disclaimer.

(21) Appl. No.: 15/617,652

(22) Filed: Jun. 8, 2017

(65) Prior Publication Data
US 2017/0265950 A1 Sep. 21, 2017

Related U.S. Application Data

(63) Continuation of application No. 14/391,659, filed as application No. PCT/US2013/037336 on Apr. 19, 2013, now Pat. No. 9,687,303.

(60) Provisional application No. 61/636,001, filed on Apr. 20, 2012.

(51) Int. Cl.
A61B 34/30 (2016.01)
A61B 34/00 (2016.01)

(52) U.S. Cl.
CPC .............. A61B 34/30 (2016.02); A61B 34/71 (2016.02); A61B 2034/305 (2016.02)

(58) Field of Classification Search
CPC .... A61B 34/30; A61B 34/71; A61B 2034/305
See application file for complete search history.

(56) References Cited

U.S. PATENT DOCUMENTS 2,286,571 A 6/1942 Pollard
2,988,237 A 6/1961 Devol
(Continued)

FOREIGN PATENT DOCUMENTS

EP 2335558 6/2011
WO WO2001/010292 A1 2/2001
(Continued)

OTHER PUBLICATIONS

Abbott et al., "Haptic virtual fixtures for robot-assisted manipulation," Robotics Research 28, Aug. 2007, 49-64.
(Continued)

Primary Examiner — Jocelin C Tanner
(74) Attorney, Agent, or Firm — Michael Best & Friedrich LLP

(57) ABSTRACT

A rotatable wrist connecting a gripper tool to the distal end of a positioning shaft. The rotatable wrist includes a wrist hub that is non-rotatably connected to the distal end of the shaft. A wrist capstan is rotatably connected to the wrist hub and non-rotatably connected to an actuatable device (e.g., a gripper). A flexible wire loop extends through the wrist hub and partially contacts the wrist capstan. Linear movement of the flexible wire loop through the shaft causes rotation of the wrist capstan due to friction between the flexible wire loop and the wrist capstan. The wrist also supports selective detachability and control of roll, pitch and roll, pitch yaw and roll according to different embodiments.

21 Claims, 7 Drawing Sheets

(56) References Cited

U.S. PATENT DOCUMENTS

| | | |
|---|---|---|
| 3,580,099 A | 5/1971 | Mosher |
| 3,727,531 A | 4/1973 | Baab |
| 3,802,743 A | 4/1974 | Hermanns |
| 4,744,264 A | 5/1988 | Milenkovic |
| 4,795,296 A | 1/1989 | Jau |
| 4,802,461 A | 2/1989 | Cho |
| 4,998,527 A | 3/1991 | Meyer |
| 5,007,907 A | 4/1991 | Nishigaki et al. |
| 5,046,375 A | 9/1991 | Salisbury, Jr. |
| 5,133,713 A | 7/1992 | Huang et al. |
| 5,201,731 A | 4/1993 | Hakky |
| 5,231,989 A | 8/1993 | Middleman et al. |
| 5,307,804 A | 5/1994 | Bonnet |
| 5,337,732 A | 8/1994 | Grundfest et al. |
| 5,345,937 A | 9/1994 | Middleman et al. |
| 5,386,741 A | 2/1995 | Rennex |
| 5,397,323 A | 3/1995 | Taylor |
| 5,410,638 A | 4/1995 | Colgate |
| 5,480,406 A | 1/1996 | Nolan et al. |
| 5,662,587 A | 9/1997 | Grundfest et al. |
| 5,749,828 A | 5/1998 | Solomon et al. |
| 5,906,591 A | 5/1999 | Dario et al. |
| 6,113,593 A | 9/2000 | Tu et al. |
| 6,197,017 B1 | 3/2001 | Brock et al. |
| 6,309,346 B1 | 10/2001 | Farhadi |
| 6,312,435 B1* | 11/2001 | Wallace ............... A61B 34/70 |
| | | 606/130 |
| 6,533,720 B1 | 3/2003 | Dhindsa |
| 6,554,844 B2 | 4/2003 | Lee et al. |
| 6,669,711 B1 | 12/2003 | Noda |
| 6,676,684 B1 | 1/2004 | Morley |
| 6,692,485 B1 | 2/2004 | Brock |
| 6,817,974 B2 | 11/2004 | Cooper et al. |
| 6,824,544 B2 | 11/2004 | Boebel et al. |
| 6,837,892 B2 | 1/2005 | Shoham |
| 6,843,793 B2 | 1/2005 | Brock et al. |
| 6,858,005 B2 | 2/2005 | Ohline et al. |
| 6,860,878 B2 | 3/2005 | Brock |
| 6,949,106 B2 | 9/2005 | Brock et al. |
| 6,971,989 B2 | 12/2005 | Yossepowitch |
| 7,021,173 B2 | 4/2006 | Stoianovici et al. |
| 7,099,745 B2 | 8/2006 | Ebert |
| 7,147,650 B2 | 12/2006 | Lee |
| 7,214,230 B2 | 5/2007 | Brock et al. |
| 7,235,089 B1 | 6/2007 | McGuckin, Jr. |
| 7,316,681 B2 | 1/2008 | Madhani et al. |
| 7,391,173 B2 | 6/2008 | Schena |
| 7,682,319 B2 | 3/2010 | Martin et al. |
| 7,699,835 B2 | 4/2010 | Lee et al. |
| 7,787,681 B2 | 8/2010 | Zhang et al. |
| 7,794,393 B2 | 9/2010 | Larsen |
| 7,822,249 B2 | 10/2010 | Garty et al. |
| 7,837,615 B2 | 11/2010 | Le et al. |
| 7,854,738 B2 | 12/2010 | Lee et al. |
| 7,887,549 B2 | 2/2011 | Wenderow et al. |
| 7,959,557 B2 | 6/2011 | Weitzner et al. |
| 8,025,635 B2 | 9/2011 | Eaton et al. |
| 8,062,214 B2 | 11/2011 | Shener et al. |
| 8,088,101 B2 | 1/2012 | Chang et al. |
| 8,114,062 B2 | 2/2012 | Muni et al. |
| 8,116,886 B2 | 2/2012 | Simaan et al. |
| 8,172,828 B2 | 5/2012 | Chang et al. |
| 8,303,576 B2 | 11/2012 | Brock |
| 8,311,626 B2 | 11/2012 | Hlavka et al. |
| 8,337,521 B2 | 12/2012 | Cooper et al. |
| 8,343,141 B2 | 1/2013 | Madhani et al. |
| 8,365,633 B2 | 2/2013 | Simaan et al. |
| 8,372,019 B2 | 2/2013 | Goldenberg et al. |
| 8,377,077 B2 | 2/2013 | Reis |
| 8,409,234 B2 | 4/2013 | Stahler et al. |
| 8,414,505 B1 | 4/2013 | Weitzner et al. |
| 8,414,598 B2 | 4/2013 | Brock et al. |
| 8,425,408 B2 | 4/2013 | Boulais et al. |
| 8,444,549 B2 | 5/2013 | Viola et al. |
| 8,460,236 B2 | 6/2013 | Roelle et al. |
| 8,480,618 B2 | 7/2013 | Wenderow et al. |
| 8,486,053 B2 | 7/2013 | Niemeyer |
| 8,498,691 B2 | 7/2013 | Moll et al. |
| 8,504,201 B2 | 8/2013 | Moll et al. |
| 8,545,551 B2 | 10/2013 | Loulmet |
| 8,551,115 B2 | 10/2013 | Steger et al. |
| 8,585,731 B2 | 11/2013 | Abbate et al. |
| 8,655,431 B2 | 2/2014 | Joos et al. |
| 8,864,757 B2 | 10/2014 | Klimovitch et al. |
| 9,333,650 B2 | 5/2016 | Bajo et al. |
| 9,549,720 B2 | 1/2017 | Simaan et al. |
| 9,591,964 B2 | 3/2017 | Choset et al. |
| 2001/0031983 A1* | 10/2001 | Brock ............... A61B 34/71 |
| | | 606/205 |
| 2002/0120252 A1 | 8/2002 | Brock et al. |
| 2003/0120305 A1 | 6/2003 | Jud et al. |
| 2003/0135204 A1 | 7/2003 | Lee et al. |
| 2004/0116906 A1 | 6/2004 | Lipow |
| 2004/0176751 A1 | 9/2004 | Weitzner et al. |
| 2005/0043718 A1 | 2/2005 | Madhani et al. |
| 2005/0054900 A1 | 3/2005 | Mawn et al. |
| 2005/0059960 A1* | 3/2005 | Simaan ............... A61B 34/70 |
| | | 606/1 |
| 2005/0228440 A1 | 10/2005 | Brock et al. |
| 2006/0036182 A1 | 2/2006 | Daniels et al. |
| 2006/0047302 A1 | 3/2006 | Ortiz et al. |
| 2006/0058861 A1 | 3/2006 | Gibson et al. |
| 2006/0079884 A1* | 4/2006 | Manzo ............... A61B 18/1442 |
| | | 606/41 |
| 2006/0156851 A1 | 7/2006 | Jacobsen et al. |
| 2006/0241414 A1 | 10/2006 | Nowlin et al. |
| 2006/0258938 A1 | 11/2006 | Hoffman et al. |
| 2007/0197939 A1 | 8/2007 | Wallace et al. |
| 2007/0225787 A1 | 9/2007 | Simaan et al. |
| 2007/0255109 A1* | 11/2007 | Stein ............... A61B 1/00087 |
| | | 600/214 |
| 2008/0009838 A1 | 1/2008 | Schena et al. |
| 2008/0033240 A1 | 2/2008 | Hoffman et al. |
| 2008/0065105 A1 | 3/2008 | Larkin et al. |
| 2008/0065108 A1 | 3/2008 | Diolaiti |
| 2008/0071288 A1 | 3/2008 | Larkin et al. |
| 2008/0114492 A1 | 5/2008 | Miegel et al. |
| 2008/0179301 A1 | 7/2008 | Garty et al. |
| 2008/0181473 A1 | 7/2008 | Garty et al. |
| 2008/0188800 A1 | 8/2008 | Bencini et al. |
| 2008/0243063 A1 | 10/2008 | Camarillo |
| 2008/0243064 A1 | 10/2008 | Stahler et al. |
| 2008/0243106 A1 | 10/2008 | Coe et al. |
| 2008/0245173 A1 | 10/2008 | Schwerin et al. |
| 2008/0249536 A1 | 10/2008 | Stahler et al. |
| 2008/0262513 A1 | 10/2008 | Stahler et al. |
| 2008/0302200 A1 | 12/2008 | Tobey |
| 2009/0054222 A1 | 2/2009 | Zhang et al. |
| 2009/0076476 A1 | 3/2009 | Barbagli et al. |
| 2009/0076521 A1 | 3/2009 | Hansen |
| 2009/0088774 A1 | 4/2009 | Swarup et al. |
| 2009/0099420 A1 | 4/2009 | Woodley et al. |
| 2009/0171151 A1 | 7/2009 | Choset et al. |
| 2009/0216083 A1 | 8/2009 | Durant et al. |
| 2009/0275818 A1 | 11/2009 | Rau et al. |
| 2009/0275857 A1 | 11/2009 | Cabiri et al. |
| 2010/0010504 A1 | 1/2010 | Simaan et al. |
| 2010/0011900 A1 | 1/2010 | Burbank |
| 2010/0016852 A1* | 1/2010 | Manzo ............... A61B 34/71 |
| | | 606/46 |
| 2010/0030377 A1 | 2/2010 | Unsworth |
| 2010/0069719 A1 | 3/2010 | Wehrheim |
| 2010/0076269 A1 | 3/2010 | Makower |
| 2010/0079308 A1 | 4/2010 | Fabre et al. |
| 2010/0099951 A1 | 4/2010 | Laby et al. |
| 2010/0125165 A1 | 5/2010 | Torii |
| 2010/0152899 A1 | 6/2010 | Chang et al. |
| 2010/0210391 A1 | 8/2010 | Dinger |
| 2010/0256558 A1 | 10/2010 | Olson et al. |
| 2010/0331857 A1 | 12/2010 | Doyle et al. |
| 2010/0331858 A1 | 12/2010 | Simaan et al. |
| 2011/0015649 A1 | 1/2011 | Anvari et al. |
| 2011/0066160 A1 | 3/2011 | Simaan et al. |
| 2011/0071541 A1 | 3/2011 | Prisco et al. |

(56) References Cited

U.S. PATENT DOCUMENTS

| | | |
|---|---|---|
| 2011/0071542 A1 | 3/2011 | Prisco et al. |
| 2011/0071544 A1 | 3/2011 | Steger et al. |
| 2011/0125165 A1 | 5/2011 | Simaan et al. |
| 2011/0160569 A1 | 6/2011 | Cohen et al. |
| 2011/0184241 A1 | 7/2011 | Zubiate et al. |
| 2011/0196419 A1 | 8/2011 | Cooper |
| 2011/0213346 A1 | 9/2011 | Morley et al. |
| 2011/0230894 A1 | 9/2011 | Simaan et al. |
| 2011/0306929 A1 | 12/2011 | Levesque et al. |
| 2011/0313243 A1 | 12/2011 | Zubiate et al. |
| 2011/0319910 A1 | 12/2011 | Roelle et al. |
| 2012/0067158 A1 | 3/2012 | Kell et al. |
| 2012/0071822 A1 | 3/2012 | Romo et al. |
| 2012/0109274 A1 | 5/2012 | Simaan et al. |
| 2012/0123395 A1 | 5/2012 | Stoy et al. |
| 2012/0241576 A1 | 9/2012 | Yu |
| 2012/0253131 A1 | 10/2012 | Malkowski et al. |
| 2012/0289946 A1 | 11/2012 | Steger |
| 2013/0012928 A1 | 1/2013 | Cooper et al. |
| 2013/0023859 A1 | 1/2013 | Malkowski |
| 2013/0090763 A1 | 4/2013 | Simaan et al. |
| 2013/0096540 A1 | 4/2013 | Cooper et al. |
| 2013/0110131 A1 | 5/2013 | Madhani et al. |
| 2013/0131868 A1 | 5/2013 | Rucker et al. |
| 2013/0165869 A1 | 6/2013 | Blumenkranz et al. |
| 2013/0165945 A9 | 6/2013 | Roelle et al. |
| 2013/0178838 A1 | 7/2013 | Malkowski |
| 2013/0190741 A1 | 7/2013 | Moll et al. |
| 2013/0197539 A1 | 8/2013 | Simaan et al. |
| 2013/0218141 A1 | 8/2013 | Hinman et al. |
| 2013/0231529 A1 | 9/2013 | John et al. |
| 2013/0269109 A1 | 10/2013 | Yu |
| 2013/0274715 A1 | 10/2013 | Chan et al. |
| 2013/0289581 A1 | 10/2013 | Yeung et al. |
| 2013/0300537 A1 | 11/2013 | Bajo et al. |
| 2013/0303945 A1 | 11/2013 | Blumenkranz et al. |
| 2013/0306112 A1 | 11/2013 | Blumenkranz |
| 2013/0338433 A1 | 12/2013 | Goldman et al. |
| 2014/0058406 A1 | 2/2014 | Tsekos |
| 2014/0221826 A1 | 8/2014 | Joos et al. |
| 2014/0316434 A1 | 10/2014 | Simaan et al. |
| 2014/0330432 A1 | 11/2014 | Simaan et al. |
| 2015/0073434 A1 | 3/2015 | Simaan et al. |
| 2017/0182659 A1 | 6/2017 | Goldman et al. |

FOREIGN PATENT DOCUMENTS

| | | |
|---|---|---|
| WO | WO2005009482 | 2/2005 |
| WO | WO2005112834 | 12/2005 |
| WO | WO2008036304 | 3/2008 |
| WO | WO2009094670 | 7/2009 |
| WO | WO2009097461 | 8/2009 |
| WO | WO2009097539 | 8/2009 |
| WO | WO2009124287 | 10/2009 |
| WO | WO2009140688 | 11/2009 |
| WO | WO2010042611 | 4/2010 |
| WO | WO2011063511 | 6/2011 |
| WO | WO2012015816 | 2/2012 |
| WO | WO2012049623 | 4/2012 |
| WO | WO2013/106664 A1 | 7/2013 |
| WO | WO2013043804 | 9/2013 |
| WO | WO2013158974 | 10/2013 |
| WO | WO2013158978 | 10/2013 |
| WO | WO2013158983 | 10/2013 |
| WO | WO2013166293 | 11/2013 |

OTHER PUBLICATIONS

Abbott et al., "Stable Forbidden-Region Virtual Fixtures for Bilateral Telemanipulation," vol. 128, No. 1, pp. 53-64, 2006.

Agrawal et al., "Control of Cable Actuated Devices using Smooth Backlash Inverse," In 2010 IEEE International Conference on Robotics and Automation, Anchorage, AK, 2010, pp. 1074-1079.

Angeles, "Automatic Computation of the Screw Parameters of Rigid-Body Motions. Part II: Infinitesimally-Separated Positions," Journal of Dynamic Systems, Measurement, and Control 108, Mar. 1986, 32-38.

Bajo et al., "A Pilot Ex-Vivo Evaluation of a Telerobotic System for Transurethral Intervention and Surveillance," In Hamlyn Symposium on Medical Robotics, 2012.

Bajo et al., "Configuration and Joint Feedback for Enhanced Performance of Multi-Segment Continuum Robots," in IEEE International Conference on Robotics and Automation, 2011, pp. 2905-2912.

Bajo et al., "Constrained Motion Control of Multisegment Continuum Robots for Transurethral Bladder Resection and Surveillance," In Accepted for publication in IEEE International Conference on Robotics and Automation (ICRA'2013).

Bajo et al., "Finding lost wrenches: Using continuum robots for contact detection and estimation of contact location," Robotics and Automation (ICRA), 2010 IEEE International Conference on DOI: 10.1109/ROBOT.2010.5509569; Publication Year: 2010, pp. 3666-3673.

Bajo et al., "Integration and Preliminary Evaluation of an Insertable Robotic Effectors Platform for Single Port Access Surgery," In International Conference on Robotics and Automation (ICRA'2012), pp. 3381-3387.

Bajo et al., "Kinematics-Based Detection and Localization of Contacts Along Multisegment Continuum Robots," IEEE Transactions on Robotics 28,2 (Apr. 2012), 291-302.

Bajo et al., "Robotic-Assisted Micro-Surgery of the Throat: the Trans-Nasal Approach," In Accepted for publication in IEEE International Conference on Robotics and Automation (ICRA'2013).

Baki et al., "Miniature tri-axial force sensor for feedback in minimally invasive surgery," In 2012 4th IEEE RAS & EMBS International Conference on Biomedical Robotics and Biomechatronics (BioRob) (Roma, Italy, Jun. 2012), IEEE, pp. 805-810.

Bhattacharyya et al., "Characterization of Constraints in Flexible Unknown Environments," In Accepted for publication in IEEE International Conference on Robotics and Automation (ICRA2013).

Bhattacharyya, "Motion Planning and Constraint Exploration for Robotics Surgery," Master Thesis, Vanderbilt University, Nashville, TN. 2011.

Birkfellner et al., "Calibration of tracking systems in a surgical environment," IEEE Transactions on Medical Imaging 17, 5 (Oct. 1998), 737-42.

Bokelberg et al., "Spatial Motion—I: Points of inflection and the differential geometry of screws," Mechanism and Machine Theory 27, 1 (1992), 1-15.

Burgner et al., "A Bimanual Teleoperated System for Endonasal Skull Base Surgery," In 2011 IEEE International Conference on Intelligent Robots and Systems (San Francisco, CA, Sep. 2011), IEEE, pp. 2517-2523.

Camarillo et al., "Configuration Tracking for Continuum Manipulators with Coupled Tendon Drive," IEEE Transactions on Robotics 25, 4 (Aug. 2009), 798-808.

Camarillo et al., "Mechanics Modeling of Tendon-Driven Continuum Manipulators," IEEE Transaction on Robotics 24,6 (2008), 1262-1273.

Camarillo et al., "Vision based 3-D shape sensing of flexible manipulators," In 2008 IEEE International Conference on Robotics and Automation (Pasadena, CA, 2008), pp. 2940-2947.

Cauberg et al., "How to improve the effectiveness of transurethral resection in nonmuscle invasive bladder cancer?" Current Opinion in Urology 2 19, 5 (2009), 504-510.

Chan et al., "A Weighted Least-Norm Solution Based Scheme for Avoiding Joint Limits for Redundant Joint Manipulators," IEEE Transaction on Robotics and Automation 11,2 (1995), 286-292.

Chen et al., "Development of a Robotically-based Automated Biodosimetry Tool for Highthroughput Radiological Triage," accepted in International Journal of Biomechatronics and Biomedical Robotics (IJBBR), vol. 1, No. 2 pp. 115-125, 2010.

Chirikjian et al., "A Modal Approach to Hyper-Redundant Manipulator Kinematics," IEEE Transaction on Robotics and Automation 10, 3 (1994), 343-354.

(56) References Cited

OTHER PUBLICATIONS

Chirikjian et al., "An obstacle avoidance algorithm for hyper-redundant manipulators," In Proceedings, IEEE International Conference on Robotics and Automation (1990), IEEE Comput. Soc. Press, pp. 625-531.
Croom et al., "Visual Sensing of Continuum Robot Shape Using Self-Organizing Maps," in 2010 IEEE International Conference on Robotics and Automation (Anchorage, AK, 2010), pp. 4591-4596.
De Luca et al., "Collision Detection and Safe Reaction with the DLR-III Lightweight Manipulator Arm," In 2006 IEEE/RSJ International Conference on Intelligent Robots and Systems (Beijing, China, 2006), pp. 1623-1630.
De Luca et al., "Modeling of Robots in Contact with a Dynamic Environment," IEEE Transaction on Robotics and Automation 10,4 (1994), 542-548.
Debus et al., "Contact State Estimation using Multiple Model Estimation and Hidden Markov Models," The International Journal of Robotics Research 23, 4-5 (2004), 399-413.
Degani et al., "Highly Articulated Robotic Probe for Minimally Invasive Surgery," In 2006 IEEE International Conference on Robotics and Automation (Orlando, FL, USA, 2006), pp. 4167-4172.
Dimaio, "da Vinci and Beyond," In 2010 IEEE International Conference on Robotics and Automation Workshop on Medical Cyber-Physical Systems (Anchorage, AK, 2010).
Ding et al., "Design and Coordination Kinematics of an Insertable Robotic Effectors Platform for Single-Port Access Surgery," IEEE/ASME Transactions on Mechatronics (2012), 1-13.
Ding et al., "Design, Simulation and Evaluation of Kinematic Alternatives for Insertable Robotic Effectors Platforms in Single Port Access Surgery," In 2010 IEEE International Conference on Robotics and Automation (Anchorage, AK, 2010), pp. 1053-1058.
Dupont et al., Design and Control of Concentric-Tube Robots, IEEE Transaction on Robotics 26, 2 (2010), 209-225.
Eberman et al., "Determination of Manipulator Contact Information from Joint Torque Measurements," In Experimental Robotics I, vol. 139. Springer, 1990, pp. 463-473.
Featherstone et al., "A General Contact Model for Dynamically-Decoupled Force/Motion Control," In 1999 IEEE International Conference on Robotics and Automation (1999), No. May, pp. 3281-3286.
Featherstone, "Modeling and Control of Contact Between Constrained Rigid Bodies," IEEE Transaction on Robotics and Automation 20, 1 (2004), 82-92.
Fine et al., "A novel dual-arm dexterous ophthalmic microsurgical robot: applications for retinal vascular cannulation and stent deployment," In American Society of Retinal Specialists, Retina congress 2009, New York, NY, Sep. 4-Oct. 4.
Fine et al., "Could Robots Ever Do Retina Surgery?" Review of Ophthalmology, vol. 17, No. 5, Issue: May 1, 2010.
Garty et al., "Development of an ultrahigh-throughput robotically-based biodosimetry workstation using in-situ assays," In 13th International Congress of Radiation Research, San Francisco, California, Jul. 8-12, 2007.
Godage et al., "Shape Function-Based Kinematics and Dynamics for Variable Length Continuum Robotic Arms," 2011 IEEE International Conference on Robotics and Automation (May 9-13, 2011).
Goldman et al., "Algorithms for Autonomous Exploration and Estimation in Compliant Environments," Robotica, 31(1), 71-88, 2013.
Goldman et al., "Compliant Motion Control for Continuum Robots with Intrinsic Actuation Sensing," in IEEE International Conference on Robotics and Automation, 2011, pp. 1126-1132.
Goldman et al., "Design and Performance Evaluation of a Minimally Invasive Telerobotic Platform for Transurethral Surveillance and Intervention," IEEE Transactions on Biomedical Engineering, 60(4), 918-925, 2013.
Goldman et al., "Rapidly Deployable Telerobotic Slave for Transurethral Exploration and Intervention," In presented in the 2011 Annual Engineering and Urology Society annual meeting, May 14, 2011, Washington, DC.
Goldman, "Analysis, Algorithms, and Control for Intelligent Surgical Exploration and Intervention," Phd Thesis, Columbia University (graduated with distinction) 2011.
Gravagne et al., "Good Vibrations: A Vibration Damping Setpoint Controller for Continuum Robots," Proceedings of the 2001 IEEE International Conference on Robotics & Automation (May 21-26, 2001).
Gravagne et al., "Kinematic Transformations for Remotely-Actuated Planar Continuum Robots," In 2000 IEEE International Conference on Robotics & Automation (San Francisco, 2000), No. April, pp. 19-26.
Gravagne et al., "Manipulability, Force, and Compliance Analysis for Planar Continuum Manipulators," IEEE Transactions on Robotics and Automation, vol. 18, No. 3 (Jun. 2002).
Guthart et al., "The IntuitiveTM Telesurgery System: Overview and Application," In 2000 IEEE International Conference on Robotics and Automation (2000), pp. 618-621.
Haddadin et al., Collision Detection and Reaction: A Contribution to Safe Physical Human-Robot Interaction. In 2008 IEEE/RSJ International Conference on Intelligent Robots and Systems (Nice, France, 2008), pp. 3356-3363.
Hamid et al., "Design and Synthesis of Wire-Actuated Universal-Joint Wrists for Surgical Application," In 2009 IEEE International Conference on Robotics and Automation, pp. 1807-1831. Kobe, Japan.
Hannan et al., "Kinematics and the Implementation of an Elephant's Trunk Manipulator and Other Continuum Style Robots," Journal of Robotic Systems 20, 2 (2003), 45-63.
Harris et al., "Experiences with Robotic Systems for Knee Surgery," vol. 1205, J. Troccaz, E. Grimson, and R. Mosges, Eds. Springer, 1997, pp. 757-766.
Hayward, "Fast Collision Detection Scheme by Recursive Decomposition of a Manipulator Workspace," Proceedings IEEE International Conference on Robotics and Automation, vol. 3 (1986).
Herrell et al., "Toward Image-Guided Robotic Surgery: System Validation," J Urol. Feb. 2009; 181(2): 783-9 Discussion 789-90. Epub Dec. 16, 2008.
Hillel et al., "Applications of Robotics for Laryngeal Surgery," Otolaryngologic Clinics of North America, Nasir Bhatti & Ralph P. Tufano Eds., vol. 41, Issue 4, pp. 781-791, doi:0.1016/j.otc.2008.01.021, Aug. 2008.
Ho et al., "Robot Assisted Knee Surgery," IEEE Engineering in Medicine and Biology Magazine 14, 3 (1995), 292-299.
Hogan, "Impedance Control: An Approach to Manipulation: Part I Theory," Journal of Dynamic Systems, Measurement, and Control 107, 1 (1985), 1.
Howell, "Compliant Mechanisms," Wiley-Interscience, 2001.
IKITS et al., "An Improved Calibration Framework for Electromagnetic Tracking Devices," In 2001 IEEE Virtual Reality (Yokohama, Japan, 2001), IEEE Comput. Soc, pp. 63-70.
Ikuta et al. "Development of remote micro-surgery robot and new surgical procedure for Jeep and narrow space," In 2003 IEEE International Conference on Robotics and Automation (Taipei, Taiwan, 2003), vol. 1, IEEE, pp. 1103-1108.
International Search Report and Written Opinion for PCT Application No. PCT/US2013/021167 dated Mar. 22, 2013.
International Search Report and Written Opinion for PCT Application No. PCT/US2013/037336 dated Jul. 25, 2013.
International Search Report and Written Opinion for PCT Application No. PCT/US2013/037346 dated Aug. 27, 2013.
International Search Report and Written Opinion for PCT Application No. PCT/US2013/037353 dated Aug. 19, 2013.
International Search Report and Written Opinion for PCT Application No. PCT/US2013/039280 dated Aug. 20, 2013.
Jones "Kinematics for Multisection Continuum Robots," IEEE Transactions on Robotics, vol. 22, No. 1 (Feb. 2006), 43-57.
Kapoor et al., "Telemanipulation of Snake-Like Robots for Minimally Invasive Surgery of the Upper Airway," in MICCAI 2006 workshop on medical robotics, 2006.

(56) References Cited

OTHER PUBLICATIONS

Kapoor et al., "A Constrained Optimization Approach to Virtual Fixtures for Multi-Handed Tasks," In IEEE International Conference on Robotics and Automation (Pasadena, CA, 2008), pp. 3401-3406.

Kapoor et al., "A System for Speed and Torque Control of DC Motors with Application to Small Snake Robots," 2004.

Kapoor et al., "Spatial Motion Constraints for Robot Assisted Suturing using Virtual Fixtures," 2005, vol. 3750, pp. 89-96.

Kapoor et al., "Suturing in Confined Spaces: Constrained Motion Control of a Hybrid 8-DoF Robot", in IEEE Conference on Advanced Robotics, 2005, pp. 452-459.

Kesner et al., "Design and Control of Motion Compensation Cardiac Catheters," In 2010 IEEE International Conference on Robotics and Automation (Anchorage, AK, 2010), pp. 1059-1065.

Kesner et al., "Force Control of Flexible Catheter Robots for Beating Heart Surgery," In 2011 IEEE International Conference on Robotics and Automation (Shanghai, China, Jan. 2011), pp. 1589-1594.

Kesner et al., S. B., Howe, R. D., and Member, S. Position Control of Motion Compensation Cardiac Catheters. IEEE Transaction on Robotics 27, 6 (2011), 1045-1055.

Khatib, "A Unified Approach for Motion and Force Control of Robot Manipulators: The Operational Space Formulation," IEEE Journal of Robotics and Automation 3,1 (1987), 43-53.

Kragic et al., "Human-Machine Collaborative Systems for Microsurgical Applications," The International Journal of Robotics Research 24, 9 (Sep. 2005), 731-741.

Kwartowitz, "Towards Image Guided Robotic Surgery: Multi-Arm Tracking Through Hybrid Localization," Int J Comput Assist Radio! Surg. May 2009;4(3):281-6. Epub Mar. 19, 2009.

Lawson et al., "Transoral robotic surgery for the management of head and neck tumors: learning curve," European archives of oto-rhino-laryngology: official journal of the European Federation of Oto-Rhino-Laryngological Societies (EUFOS): affiliated with the German Society for Oto-Rhino-Laryngology—Head and Neck Surgery 268, 12 (Dec. 2011), 1795-801.

Li et al. "Spatial Motion Constraints in Medical Robot Using Virtual Fixtures Generated by Anatomy," 2004, pp. 1270-1275.

Lipkin et al., "Hybrid Twist and Wrench Control for a Robotic Manipulator," Transaction of the ASME 110 (1988), 138-144.

Lock et al., "Friction Modeling in Concentric Tube Robots," In 2011 IEEE International Conference on Robotics and Automation (Shanghai, China, Jan. 2011), pp. 1139-1146.

Lumelsky et al., "Real-Time Collision Avoidance in Tele-operated Whole-Sensitive Robot Arm Manipulators," IEEE Transactions on Systems, Man, and Cybernetics 23, 1 (1993), 194-203.

Ma et al., "An obstacle avoidance scheme for hyper-redundant manipulators-global motion planning in posture space," In Proceedings of International Conference on Robotics and Automation (1997), vol. 1, IEEE, pp. 161-166.

Mahvash et al., "Friction Compensation for a Force-Feedback Telerobotic System," In 2006 IEEE International Conference on Robotics and Automation (Orlando, FL, 2006), No. May, pp. 3268-3273.

Mahvash et al., "Mechanics of dynamic needle insertion into a biological material," IEEE transactions on bio-medical engineering 57, 4 (Apr. 2010), 934-43.

Mahvash et al., "Stiffness Control of a Continuum Manipulator in Contact with a Soft Environment," The 2010 IEEE/RSJ International Conference on Intelligent Robots and Systems (Oct. 18-22, 2010).

Mahvash et al., "Stiffness Control of Surgical Continuum Manipulators," IEEE Transaction on Robotics 27, 2 (2011), 334-345.

Mason et al.,"Robot Hands and the Mechanics of Manipulation," MIT Press, Cambridge, MA, 1985.

Mason, "Compliance and Force Control for Computer Controlled Manipulators," IEEE Transaction on Systems, Vlan, and Cybernetics smc-11, 6 (1981), 418-432.

Matsumoto et al., "Collision Detection of Manipulator Based on Adaptive Control Law," In 2001 IEEE/ASME International Conference on Advanced Intelligent Mechatronics (Como, Italy, 2001), pp. 177-182.

Nakamura, "Advanced Robotics: Redundancy and Optimization," Addison-Wesley Longman Publishing Co., Inc., Boston, MA, USA, 1990.

Park et al., "Robot Multiple Contact Control," Robotica 26, 05 (2008), 667-677.

Penning et al., "Towards Closed Loop Control of a Continuum Robotic Manipulator for Medical Applications," In 2011 IEEE International Conference on Robotics and Automation (Shanghai, China 2011), pp. 4822-4827.

Petrovskays et al., "Probabilistic Estimation of Whole Body Contacts for Multi-Contact Robot Control," In 2007 IEEE International Conference on Robotics and Automation (Rome, 2007), No. c, pp. 568-573.

Phee et al., "Robotic system for no-scar gastrointestinal surgery," The international journal of medical robotics + computer assisted surgery: MRCAS 4, 1 (Mar. 2008), 15-22.

Piccigallo et al., "Design of a Novel Bimanual Robotic System for Single-Port Laparoscopy," IEEE/ASME Transaction on Mechatronics 15, 6 (2010), 871-878.

Pickens et al., "Preliminary Testing of a Transurethral Dexterous Robotic System for Bladder Resection," In 27th EUS Annual Meeting, pp. 65. Atlanta, GA 2012.

Pile et al., "Algorithms and Design Considerations for Robot Assisted Insertion of Perimodiolar Electrode Arrays," In 2011 IEEE International Conference on Robotics and Automation. Shanghai, China 2011.

Pile et al., "Characterization of Friction and Speed Effects and Methods for Detection of Cochlear Implant Electrode Tip Foldover," In Accepted for publication in IEEE International Conference on Robotics and Automation (ICRA'2013).

Pile et al., "Speed Dependence of Insertion Forces During CI Electrode Insertion," In Presented at the 12th Annual Conference on Cochlear Implants and other Implantable Auditory Technologies CI'2012, Baltimore, MD, May 3-5, 2012.

Railbert et al., "Hybrid Position/Force Control of Manipulators," Journal of Dynamic Systems, Measurement, and Control 103, 2 (1981), 126.

Reichert et al., "Robotic insertion of cochlear implant electrodes to minimize cochlear trauma," In 6th European Congress of Oto-Rhino-Laryngology, Head and Neck Surgery., Vienna, Austria, Jun. 2007.

Reiter et al., "A Learning Algorithm for Visual Pose Estimation of Continuum Robots," In 2011 IEEE/RSJ International Conference on Intelligent Robots and Systems (San Francisco, CA, USA, 2011), pp. 2390-2396.

Reiter et al., "Learning-Based Configuration Estimation of a Multi-Segment Continuum Robot," In the Fourth IEEE RAS/EMBS International Conference on Biomedical Robotics and Biomechatronics (Roma, Italy, 2012), p. accepted.

Rivera-Serrano et al., "A transoral highly flexible robot: Novel technology and application," The Laryngoscope 122, 5 (May 2012), 1067-71.

Robinson et al., "Continuum robots—a state of the art," In 1999 IEEE International Conference on Robotics and Automation (Detroit, MI, USA, 1999), vol. 4, IEEE, pp. 2849-2854.

Roland et al., "Progress Towards a Robotically Inserted Cochlear Implant Electrode," In 12th Symposium on Cochlear Implants in Children, Seattle 2009.

Rosenberg, "Virtual fixtures: Perceptual tools for telerobotic manipulation," in Proceedings of IEEE Virtual Reality Annual International Symposium, 1993, pp. 76-82.

Rucker et al., "Deflection-Based Force Sensing for Continuum Robots: A Probabilistic Approach," In 2011 IEEE/RSJ International Conference on Intelligent Robots and Systems (2011), pp. 3764-3769.

Rucker et al., "Geometrically Exact Model for Externally Loaded Concentric-Tube Continuum Robots," IEEE Transaction on Robotics 26, 5 (2010), 769-780.

(56) References Cited

OTHER PUBLICATIONS

Saito, "Transurethral en bloc resection of bladder tumors," The Journal of Urology 166,6 (Dec. 2001), 2148-50.
Salerno et al., "Design Considerations for a Minimally Invasive High-Throughput Automation System for Radiation Biodosimetry," In IEEE Conference on Automation Science and Engineering, pp. 846-852. Scottsdale, AZ, USA 2007.
Salisbury, Active stiffness control of a manipulator in cartesian coordinates. In 1980 19th IEEE Conference on Decision and Control including the Symposium on Adaptive Processes (1980), pp. 95-100.
Seibold et al., "Prototype of Instrument for Minimally Invasive Surgery with 6-Axis Force Sensing Capability," In Proceedings of the 2005 IEEE International Conference on Robotics and Automation (Barcelona, Spain, 2005), 496-501, Ed., IEEE, pp. 496-501.
Sen et al., "Enabling technologies for natural orifice transluminal endoscopic surgery (N.O.T.E.S) using robotically guided elasticity imaging," In Proceeding of SPIE Medical Imaging 2012, pp. 83161Y1-83161Y8.
Sentis et al., "Compliant Control of Multicontact and Center-of-Mass Behaviors in Humanoid Robots," IEEE Transactions on Robotics 26, 3 (Jun. 2010), 483-501.
Shen et al., "A Robotic-controlled Intraocular OCT Probe," In 2013 The Association for Research in Vision and Ophthalmology Annual Conference (ARVO'2013).
Siciliano et al., "Robotics: Modelling, Planning, and Control," 2009.
Simaan et al. "Design and Integration of a Telerobotic System for Minimally Invasive Surgery of the Throat," International Journal of Robotics Research (IJRR) special issue on medical robotics. doi: 10.1177/0278364908104278, vol. 28, No. 9, 1134-1153 , 2009.
Simaan et al., "A Dexterous System for Laryngeal Surgery—Multi-Backbone Bending Snake-like Slaves for Teleoperated Dexterous Surgical Tool Manipulation." pp. 351-357, 2004.
Simaan et al., "A Dual-Arm Workstation for Intraocular Dexterity-Enhanced Microsurgery of the Eye and In-Organ Dexterity Enhancement and Manipulation of Suspended Organs," 2006.
Simaan et al., "Design Considerations of New Six Degrees-of-Freedom Parallel Robots," In IEEE International Conference on Robotics and Automation (ICRA'1998), pp. 1327-1333.
Simaan et al., "Geometric Interpretation of the Derivatives of Parallel Robot's Jacobian Matrix with Application to Stiffness Control" ASME Journal of Mechanical Design, vol. 125, pp. 33-42., doi: 10.1115/1.1539514, 2003.
Simaan et al., "High Dexterity Snake-like Robotic Slaves for Minimally Invasive Telesurgery of the Upper Airway," MICCAI 2004 (7th International Conference on Medical Image Computing and Computer-Assisted Intervention), pp. 17-24, vol. 2, Saint Malo, France, Sep. 26-30, 2004.
Simaan et al., "Inroads towards a robotically inserted CI electrode development," In 9th European Symposium of Paediatric Cochlear Implantation, 2009.
Simaan et al., "Lessons learned using the insertable robotic effector platform (IREP) for single port access surgery," Journal of Robotic Surgery, Apr. 2013.
Simaan et al., "Minimally Invasive Surgery of the Upper Airways: Addressing the Challenges of Dexterity Enhancement in Confined Spaces," Nova Scien, R. Faust, Ed. 2007, pp. 261-280.
Simaan et al., "Robotic Study Shows that Insertion Speed Affects cochlear Implant Electrode Insertion Forces," In the 11th International Conference on Cochlear Implants and other Implantable Auditory Technologies, Stockholm, Sweden, Jun. 30-Jul. 3, 2010.
Simaan et al., "Robotic System for Steerable Cochlear Implant Insertion," In 2011 National Congress of the Italian Society of Audiology & Phoniatrics in Bari, Italy 2011.
Simaan et al., "Singularity Analysis of a Class of Composite Serial In-Parallel Robots," IEEE transactions on Robotics and Automation, vol. 17, No. 3, pp. 301-311, doi:10.1109/70.938387 Jun. 2001.
Simaan et al., "Steerable Continuum Robot Design for Cochlear Implant Surgery," In IEEE International Conference on Robotics and Automation Workshop on Snakes, Worms and Catheters: Continuum and Serpentine Robots for Minimally Invasive Surgery, May 3. 2010.
Simaan et al., "Stiffness Synthesis of a Variable Geometry Six Degrees-of-Freedom Double Planar Parallel Robot," International Journal of Robotics Research (IJRR), vol. 22, No. 9, pp. 757-775, doi: 10.1177/02783649030229005, Sep. 2003.
Simaan, "Analysis and Synthesis of Parallel Robots for Medical Applications," Master Thesis. Technion-Israel Institute of Technology, Haifa, Israel, 1999.
Simaan, "Design Considerations and Lessons Learned in Developing Systems for Single Port Access Surgery and Natural Orifice Surgery," In 34th international Conference on Engineering in Medicine and Biology Society (mini-symposium on Robotic Single-Port Surgery and Notes). San Diego, Aug. 27-31, 2012.
Simaan, "Snake-Like Units Using Flexible Backbones and Actuation Redundancy for Enhanced Miniaturization," In 2005 IEEE International Conference on Robotics and Automation (Barcelona, Spain, 2005), IEEE, pp. 3023-3028.
Simaan, "Task-Based Design and Synthesis of Variable Geometry Parallel Robots," (2002). Phd Thesis, Technion-Israel Institute of Technology, Haifa, Israel.
Sturges et al., "A flexible, tendon-controlled device for endoscopy," 1991, vol. 3, pp. 2582-2591.
Su et al., "A MRI-Guided Concentric Tube Continuum Robot with Piezoelectric Actuation: A Feasibility Study," In 2012 IEEE International Conference on Robotics and Automation, pp. 1939-1945.
Taylor et al., "Steady-hand robotic system for microsurgical augmentation," International Journal of Robotics Research, vol. 18, No. 12, pp. 1201-1210, 1999.
Torres et al., Motion Planning for Concentric Tube Robots Using Mechanics-based Models. In 2011 IEEE/RSJ International Conference on Intelligent Robots and Systems (San Francisco, CA, USA, 2011), pp. 5153-5159.
Tully et al., "Constrained Filtering with Contact Detection Data for the Localization and Registration of Continuum Robots in Flexible Environments," In 2012 IEEE International Conference on Robotics and Automation (St. Paul, MI USA, 2012).
U.S. Office action for U.S. Appl. No. 13/891,389 dated Jan. 2, 2015.
U.S. Office action for U.S. Appl. No. 14/271,418 dated May 20, 2015.
Ukai et al., "A new technique for transurethral resection of superficial bladder tumor in 1 piece.," The Journal of Urology 2 163, 3 (2000), 878-879.
Valdastri et al., "Integration of a miniaturised triaxial force sensor in a minimally invasive surgical tool," IEEE transactions on biomedical engineering 53, 11 (Nov. 2006), 2397-400.
Wagner et al., The Benefits of Force Feedback in Surgery: Examination of Blunt Dissection. Presence: Teleoperators and Virtual Environments 16, 3 (2007), 252-262.
Webster,III et al., "Design and Kinematic Modeling of Constant Curvature Continuum Robots: A Review," The International Journal of Robotics Research (Jun. 2010).
Webster,III et al., "Mechanics of Precurved-Tube Continuum Robots," IEEE Transaction on Robotics 25, 1 (2009), 67-78.
Wei et al., "A compact Two-armed Slave Manipulator for Minimally Invasive Surgery of the Throat," in IEEE RAS/EMBS International Conference on Biomedical Robotics and Biomechatronics, 2006, pp. 769-774.
Wei et al., "A Pilot Study on Using a Flexible Cannula Robot for Micro-Vascular Stenting," In IEEE International Conference on Robotics and Automation Workshop on Snakes, Worms and Catheters: Continuum and Serpentine Robots for Minimally Invasive Surgery, IEEE International Conference on Robotics and 4utomation, May 3, 2010.
Wei et al., "An Intelligent Hand-Held Microsurgical Instrument for Improved Accuracy," In 23rd Annual International Conference of the IEEE Engineering in Medicine and Biology Society (Istanbul, Turkey, 2001), pp. 25-28.

(56) References Cited

OTHER PUBLICATIONS

Wei et al., "Design and Dexterity Evaluation for a Dual-Arm Micro-Surgical Robotic System for Orbital Manipulation and Intraocular Dexterity," IEEE Transactions on Robotics, vol. 25, No. 1, pp. 147-157, 2009.

Wei et al., "Design and Theoretical Evaluation of Micro-Surgical Manipulators for Orbital Manipulation and Intraocular Dexterity," In 2007 IEEE International Conference on Robotics and Automation, pp. 3389-3395. Roma, Italy.

Wei et al., "Design of Planar Parallel Robots With Preloaded Flexures for Guaranteed Backlash Prevention," ASME Journal of Mechanisms and Robotics (JMR), doi:10.1115/1.4000522, vol. 2, No. 1, pp. 011012-1 to 011012-10, 2010.

Wei et al., "Enabling Technology for Micro-Vascular Stenting in Ophthalmic Surgery," ASME Journal of Medical Devices (JMED), vol. 4, Issue 1, 014503 (6 pages) doi:10.1115/1.4001193, 2010.

Wei et al., "Modeling, Force Sensing, and Control of Flexible Cannulas for Microstent Delivery," Journal of Dynamic Systems, Measurement, and Control 134, 4 (2012), 041004.

Wei et al., "Performance Evaluation for Multi-Arm Manipulation of Hollow Suspended Organs," IEEE Transactions on Robotics, vol. 25, No. 1, pp. 147-157, doi 10.1109/TRO.2008.2006865, 2009.

Wei, "Design and Implementation of High-Precision Hybrid Robotic Systems with Application for Ophthalmic Micro-Surgery," Phd Thesis, Department of Mechanical Engineering, Columbia University, New York City, NY 2010.

Weinstein et al., "Transoral robotic surgery: A multicenter study to assess feasibility, safety, and surgical margins," The Laryngoscope (Jul. 2012), 1-7.

Whitney, "Force Feedback Control of Manipulator Fine Motions," Journal of Dynamic Systems, Measurement, and Control 99, 2 (1977), 91.

Whitney, "Resolved Motion Rate Control of Manipulators and Human Prostheses," IEEE Transaction on Man-Machine Systems MMS-10, 2 (Jun. 1969), 47-53.

Xu et al., "A Pilot Investigation of Continuum Robots as a Design Alternative for Upper Extremity Exoskeletons," In IEEE International Conference on Robotics and Biomimetics (ROBIO'2011), pp. 656-662.

Xu et al., "Actuation Compensation for Flexible Surgical Snake-like Robots with Redundant Remote Actuation," In IEEE International Conference on Robotics and Automation, 2006, pp. 4148-4154.

Xu et al., "An Investigation of the Intrinsic Force Sensing Capabilities of Continuum Robots," IEEE Transactions on Robotics (TRO), vol. 23, No. 3 (Jun. 2008).

Xu et al., "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.

Xu et al., "Intrinsic Wrench Estimation and Its Performance Index for Multisegment Continuum Robots," IEEE Transactions on Robotics, vol. 26, No. 3, pp. 555-561, Jun. 2010.

Xu et al., "System Design of an Insertable Robotic Effector Platform for Single Port Access (SPA) Surgery," in IEEE/RSJ International Conference on Intelligent Robots and Systems, 2009, pp. 5546-5552.

Xu, "Design, Modeling and Analysis of Continuum Robots as Surgical Assistants with Intrinsic Sensory Capabilities," Phd Thesis, Columbia University 2009.

Yoshikawa, "Force Control of Robot Manipulators," In 2000 IEEE International Conference on Robotics and Automation (San Francisco, CA, USA, 2000), No. Apr., pp. 220-226.

Yu et al., "Design, Calibration and Preliminary Testing of a Robotic Telemanipulator for OCT guided Retinal Surgery," In Accepted for publication in IEEE International Conference on Robotics and Automation (ICRA2013).

Zhang et al., "A Pilot Study of Robot-Assisted Cochlear Implant Surgery Using Steerable Electrode Arrays," in International Conference on Medical Image Computing and Computer-Assisted Intervention (MICCAI '06), 2006, pp. 33-40.

Zhang et al., "Inroads towards Robot-Assisted Cochlear Implant Surgery using Steerable Electrode Arrays," Otology & Neurology special issue on Cochlear Implants, doi: 1097/MAO.0b013e3181e7117e, 2010.

Zhang et al., "Model and Parameter Identification of Friction During Robotic Insertion of Cochlear-Implant Electrode Arrays," in IEEE International Conference on Robotics and Automation, 2009, pp. 3859-3864.

Zhang et al., "Optimal Design of Under-actuated Steerable Electrode Arrays for Optimal Insertions," ASME Journal on Mechanisms and Robotics, Submitted, 2010.

Zhang et al., "Optimal Path Planning for Robotic Insertion of Steerable Electrode Arrays in Cochlear Implant Surgery," ASME Journal of Medical Devices, vol. 3, No. 1, 2009.

Zhang et al., "Path Planning and Workspace Determination for Robot-Assisted Insertion of Steerable Electrode Arrays for Cochlear Implant Surgery," Med Image Comput Comput Assist Interv. 2008;11(Pt 2):692-700.

Zhang, "Design of Steerable Electrode Arrays and Optimal Insertion Path Planning for Robot-Assisted Cochlear Implant Surgeries," Phd Thesis, Department of Mechanical Engineering, Columbia University, New York City, NY 2010.

Zhou et al., "Linear Velocity and Acceleration Estimation of 3 DOF Haptic Interface," In IEEE International Workshop on Haptic Audio Visual Environments and their Application (HAVE 2008) (Ottawa, Canada, 2008), pp. 137-142.

Abiko et al., "On-line parameter identification of a payload handled by flexible based manipulator," in 2004 IEEE/RSJ International Conference on Intelligent Robots and Systems (IROS) (IEEE Cat. No. 04CH37566), 2004, vol. 3, pp. 2930-2935.

Adami et al., "Primary and secondary prevention in the reduction of cancer morbidity and mortality," European Journal of Cancer, 2001, vol. 37, pp. 118-127.

Adunka et al., "Development and Evaluation of an Improved Cochlear Implant Electrode Design for Electric Acoustic Stimulation," Laryngoscope, 2004, vol. 114, pp. 1237-1241.

Adunka et al., "Preservation of basal inner ear structures in cochlear implantation," Orl J Otorhinolaryngol Relat Spec, 2004, vol. 66, pp. 306-312.

Agarwal et al., "Retinal imaging using a 25-gauge OCT endoprobe through vitreous and vitreous substitutes," in Association for Research in Vision and Ophthalmology (ARVO) Annual Meeting, 2013.

Almony et al., "Techniques, rationale, and outcomes of internal limiting membrane peeling," Retina, 2012, 32(5):877-91.

Anderson et al., "Tensor-arm Manipulator Design," ASME J. Mech. Eng., 1967, vol. 89, No. 8, p. 54.

Anon, "Going Where Others Have Not Gone Before: The Revolutionary Spine Robot Has Now Entered the Very Competitive Spray Painting Market," Industrial Robot, vol. 12, pp. 36-37, 1985.

Anonymous, "Argon laser photocoagulation for macular edema in branch vein occlusion. The Branch Vein Occlusion Study Group," Am J Ophthalmol, 1984, vol. 98, pp. 271-282.

Aoki et al., "Development of Slime Robot Using Bridle Bellows," J. Robot. Mechatron., vol. 16, No. 3, pp. 286-292, 2004.

Aramaki et al., "Tube type micro manipulator using shape memory alloy (SMA)," in Proc. IEEE 6th Int. Symp. Micro Mach. Human Science, Nagoya, Japan, 1995, pp. 115-120.

Asai et al., "Micro-Neurosurgical System in the Deep Surgical Field," in MICCA 2004 (7th International Conference on Medical Image Computing and Computer-Assisted Intervention), 2004, pp. 33-40.

Ascari et al., "A New Active Microendoscope for Exploring the Sub-arachnoid Space in the Spinal Cord," International Conference on Robotics and Automation, 2003, pp. 2657-2662.

Babbar et al., "Robot-assisted urologic surgery in 2010—Advancements and future outlook," Urol. Ann., 2011, vol. 3, No. 1, pp. 1-7.

Bailly et al., "Modeling and control of a hybrid continuum active catheter for aortic aneurysm treatment," in Proceedings of the 2005 IEEE International Conference on Robotics and Automation, IEEE, 2005, pp. 924-929.

(56) References Cited

OTHER PUBLICATIONS

Bajo et al., "Robotic-Assisted Micro-Surgery of the Throat: the Trans-Nasal Approach," in IEEE International Conference on Robotics and Automation, 2013, pp. 232-238.
Bajo, "Control, Sensing, and Telemanipulation of Surgical Continuum Robots," Vanderbilt University, 2013, 217 pages.
Ballay et al., "Steady-state response audiometry in a group of patients with steeply sloping sensorineural hearing loss," Laryngoscope, 2005, vol. 115, pp. 1243-1246.
Barreto et al., "Automatic camera calibration applied to medical endoscopy," in BMVC 2009—20th British Machine Vision Conference, 2009, pp. 1-10.
Battmer et al., "Evaluation of the neural response telemetry (NRT) capabilities of the nucleus research platform 8: initial results from the NRT trial," Int J Audiol, vol. 43, pp. 10-15, 2004.
Benway et al., "Robot-Assisted Partial Nephrectomy: An International Experience," European Urology, 2010, vol. 57, pp. 815-820.
Bookstein, "Principal warps: thin-plate splines and the decomposition of deformations," IEEE Trans. Pattern Anal. Mach. Intell., 1989, vol. 11, 567-585.
Box et al., "Robot-Assisted NOTES Nephrectomy: Initial Report," Journal of Endourology, 2008, vol. 22, pp. 503-506.
Box et al., "Robotic radical prostatectomy: long-term outcomes," Current Opinion in Urology, 2008, vol. 18, pp. 173-179.
Braganza et al., "A Neural Network Controller for Continuum Robots," IEEE Trans. Robot., 2007, vol. 23, No. 6, pp. 1270-1277.
Brandt et al., "A Compact Robot for Image Guided Orthopedic Surgery: Concept and preliminary Results," in Lecture Notes in Computer Science (LNCS) vol. 1205, J. Troccaz, E. Grimson, and R. Mosges, Eds.: Springer, 1997, 767-776.
Brandt et al., "CRIGOS: A compact robot for image-guided orthopedic surgery," IEEE Transactions on Information Technology in Biomedicine, 1999, vol. 3, pp. 252-260.
Brown et al., "A novel GJB2 (connexin 26) mutation, F142L, in a patient with unusual mucocutaneous findings and deafness," J Invest Dermatol, 2003, vol. 121, pp. 1221-1223.
Burgner et al., "A Telerobotic system for transnasal surgery," IEEE/ASME Transactions on Mechatronics, 2014, vol. 19, No. 3, pp. 996-1006.
Burgner-Kahrs et al., "Continuum robots for medical applications: A survey," IEEE Transactions on Robotics, 2015, vol. 31, No. 6, pp. 1261-1280.
Buss et al., "Selectively Damped Least Squares for Inverse Kinematics," 2005, vol. 10, No. 3, pp. 37-49.
Cahill et al., "The effect of arteriovenous sheathotomy on cystoid macular oedema secondary to branch retinal vein occlusion," Br J Ophthalmol, 2003, vol. 87, pp. 1329-1332.
Cahill et al., "Intraperitoneal virtual biopsy by fibered optical coherence tomography (OCT) at natural orifice transluminal endoscopic surgery (NOTES)," J. Gastrointest. Surg., 2010, vol. 14, No. 4, pp. 732-738.
Cannon et al., "Port Placement Planning in Robot-Assisted Coronary Attery Bypass," IEEE Transactions on Robotics and Automation, 2003, vol. 19, pp. 912-917.
Carpentier et al., "Residual internal limiting membrane after epiretinal membrane peeling: results of the Pan-American Collaborative Retina Study Group," Retina, 2013, pp. 2026-2031.
Cassilly et al., "Optimizing motion scaling and magnification in robotic surgery," Surgery, 2004, vol. 136, No. 2, pp. 291-294.
Cavusoglu et al., "Robotics for Telesurgery: Second Generation Berkley/UCSF Laprascopic Telesurgical Workstation and Looking towards the Future Applications," in 39th Allerton Conference on Communication, Control and Computing Monticello, Italy, 2001.
Chang et al., "LIBSVM: A Library for Support Vector Machines," 2001. [Online]. Available: http://www.csie.ntu.edu.tw/cjlin/libsvm.
Chatzilias et al., "Robotic control in hand-assisted laparoscopic nephrectomy in humans—A pilot study," in Conference Proceedings—26th Annual International Conference of the IEEE Engineering in Medicine and Biology Society, EMBC 2004, Sep. 1-Sep. 5, 2004, San Francisco, CA, United states, 2004, pp. 2742-2745.
Chen et al., "Evaluation of trajectories and contact pressures for the straight nucleus cochlear implant electrode array—a two dimensional application of finite element analysis," Medical Engineering & Physics, 2003, vol. 25, pp. 141-147.
Chen et al., "Identification of the Flexible Actuator of a Clonoscope," IEEE/RSJ International Conference on Intelligent Robots and Systems, 2003, pp. 3355-3360.
Chen et al., "Linkage of otosclerosis to a third locus (OTSC3) on human chromosome 6p21.3-22.3," J Med Genet, 2002, vol. 39, pp. 473-477.
Chen et al., "Sensor-based guidance control of a continuum robot for a semi-autonomous colonoscopy," Robot. Autonom. Syst., 2009, vol. 57, No. 6-7, pp. 712-722.
Chen et al., "Treatment of fingertip degloving injury using the bilaterally innervated sensory cross-finger flap," Ann. Plast. Surg., 2014, vol. 73, pp. 645-651.
Cheung et al., "Minimally invasive cystectomy approaches in the treatment of bladder cancer," Expert Rev. Anticancer Ther., 2012, vol. 12, No. 6, pp. 733-741.
Chiaverini et al., "Review of the damped least-squares inverse kinematics with experiments on an industrial robot manipulator," IEEE Trans. Control Syst. Technol., 1994, vol. 2, No. 2, pp. 123-134.
Chirikjian et al., "A Geometric Approach to Hyper-Redundant Manipulator Obstacle Avoidance," ASME Journal of Mechanical Design, 1992, vol. vol. 114, pp. 580-585.
Chirikjian et al., "A Modal Approach to Hyper-Redundant Manipulator Kinematics," IEEE Transactions on Robotics and Automation, vol. 10, pp. 343-354, 1994.
Chirikjian et al., "Design and Experiments with a 30 DOF Robot," IEEE International Conference on Robotics and Automation, 1993, pp. 113-119.
Chirikjian et al., "Kinematically Optimal Hyper-Redundant Manipulator Configurations," IEEE Transactions on Robotics and Automation, 1995, vol. 11, pp. 794-806.
Chirikjian, "General Methods for Computing Hyper-Redundant Manipulator Inverse Kinematics," IEEE/RSJ International conference on Intelligent Robots and Systems (IROS), 1993, pp. 1067-1073.
Cho et al., "Macro-micro manipulation with visual tracking and its application to wheel assembly," Int. J. Control. Autom. Syst., 2005, vol. 3, No. 3, pp. 461-468.
Chung et al., "Arteriovenous crossing sheathotomy versus intravitreal triamcinolone acetonide injection for treatment of macular edema associated with branch retinal vein occlusion," Graefes Arch Clin Exp Ophthalmol, 2008, vol. 246, pp. 967-974.
Cianchetti et al., "Stiff-flop surgical manipulator: Mechanical design and experimental characterization of the single module," in 2013 IEEE/RSJ International Conference on Intelligent Robots and Systems, IEEE, 2013, pp. 3576-3581.
Cohen et al., "Improved and Simplified Methods for Specifying Positions of the Electrode bands of a Cochlear Implant Array," The American Journal of Otology, 1996, vol. 17, pp. 859-865.
Cohen et al., "Surgical technique for the Nucleus Contour cochlear implant," Ear Hear, 2002, vol. 23, pp. 59S-66S.
Coman et al., "Prospective evaluation of the clinical utility of endoscopic submucosal dissection (ESD) in patients with barretts esophagus: A western center experience," Endoscopy International Open, 2016, E715-E721.
Compare et al., "Screening for and surveillance of gastric cancer," World journal of gastroenterology: WJG, 2014, vol. 20, No. 38, p. 13681-13691.
Conrad et al., "Robotic Calibration Issues: Accuracy, Repeatability and Calibration," in 8th Mediterranean Conference on Control & Automation, 2000, pp. 17-19.
Coscas et al., "Management of retinal vein occlusion—consensus document," 11 Ophthalmologica, 2011, vol. 226, pp. 4-28.
Creighton et al., "Safe Superconducting Current Discharge for the Magnetic Stereotaxis System," IEEE Transactions on Magnetics, 1999. vol. 35, pp. 4285-4290.
Dahiya et al., "Tactile Sensing From Humans to Humanoids," IEEE Trans. Robot., 2010, vol. 26, No. 1, pp. 1-20.

(56) References Cited

OTHER PUBLICATIONS

Dandurand, "The Rigidity of Compound Spatial Grid," Structural Topology, 1984, vol. 10, pp. 41-56.
Dario et al., "A Miniature Steerable End-Effector for Application in an Integrated System for Computer-Assisted Arthroscopy," IEEE International Conference on Robotics and Automation, 1997, pp. 1573-1579.
Dario et al., "Development and In Vitro Testing of a Miniature Robotic System for Comuter-Assisted Clonoscopy," 1999, vol. 4, pp. 1-14.
Dario et al., "Robotics as a future and emerging technology: Biomimetics, cybernetics, and neuro-robotics in European projects," IEEE Robotics and Automation Magazine, 2005, vol. 12, pp. 29-45.
Dasgupta et al., "The Stewart Platforms Manipulator: A Review," In Mechanism and Machine Theory, 2000, vol. 35, pp. 15-40.
D'Attansio et al., "A Semi-Automatic Handheld Mechatronic Endoscope with Collision-Avoidance Capabilities," IEEE International Conference on Robotics & Automation, 2000, pp. 1586-1591.
Davies et al., "Robotic control in knee joint replacement surgery," Proceedings of the Institution of Mechanical Engineers, Part H: Journal of Engineering in Medicine, 2007, vol. 221, pp. 71-80.
Deklaj et al., "Laparoscopic radical versus laparoscopic partial nephrectomy for clinical T1bN0M0 renal tumors: comparison of perioperative, pathological, and functional outcomes," Journal of endourology / Endourological Society, 2010, vol. 24, pp. 1603-1607.
Del Giudice et al., "Design considerations for continuum robot actuation units enabling dexterous transurethral bladder cancer resection," in ASME 2016 International Design Engineering Technical Conferences and Computers and Information in Engineering Conference. American Society of Mechanical Engineers, 2016, pp. V05AT07A030-1-V05AT07A030-10.
Della Santa et al., "Steerable Microcatheters Actuated by Embedded Conducting Polymer Structures," Journal of Intelligent Material Systems and Structures, 1996, vol. 7, pp. 292-300.
Deo et al., "Robot subtask performance with singularity robustness using optimal damped least-squares," in Proceedings 1992 IEEE International Conference on Robotics and Automation, 1993, pp. 434-441.
Dhingra et al., A Gröbner-Sylvester Hybrid Method for Closed-Form Displacement Analysis of Mechanisms, ASME Journal of Mechanical Design, 2000, vol. 122, pp. 431-438.
Dietmaier, The Stewart-Gough Platform of General Geometry Can Have 40 Real Postures, in Advances in Robot Kinematics—Analysis and Control (ARK-1998): Kluwer Academic Publishers, 1998, pp. 7-16.
Dogangil et al., "A review of medical robotics for minimally invasive soft tissue surgery," Proceedings of the Institution of Mechanical Engineers, Part H: Journal of Engineering in Medicine, 2010, vol. 224, pp. 653-679.
Ebert-Uphoff et al., "Inverse Kinematics of Discretely Actuated Hyper-Redundant Manipulators Using Workspace Densities," IEEE Int. Conf. on Robotics and Automation, 1996, pp. 139-145.
Egeland, "Task-space tracking with redundant manipulators," IEEE J. Robot. Autom., 1987, vol. 3, No. 5, pp. 471-475.
Entsfellner et al., "Micro-Macro Telemanipulator for Middle-Ear Microsurgery," in Robotics; Proceedings of ROBOTIK 2012; 7th German Conference on, 2012, pp. 395-398.
Eshraghi et al., "Comparative Study of Cochlear Damage with Three Perimodiolar Electride Designs," The Laryngeoscope, 2003, vol. 113, pp. 415-419.
Fadda et al., "Computer Assisted Planning for Total Knee Arthoplasty," in Lecture Notes in Computer Science (LNCS) vol. 1205, J. Troccaz, E. Grimson, and R. Mosges, Eds.: Springer, 1997, 619-628.
Falkenhahn et al., "Dynamic modeling of bellows-actuated continuum robots using the euler—lagrange formalism," IEEE Transactions on Robotics, 2015, vol. 31, No. 6, pp. 1483-1496.
Farah et al., "Dyes in ocular surgery: principles for use in chromovitrectomy," Am J Ophthalmol, 2009, vol. 148, pp. 332-340.
Faugere et al., "Combinatorial Classes of Parallel Manipulators," Mechanism and Machine Theory, 1995, vol. 6, pp. 765-776.
Ficarra et al., "Evidence from robot-assisted laparoscopic radical prostatectomy: a systematic review," Eur. Urol., 2007, vol. 51, No. 1, discussion 56, pp. 45-56.
Fichter, "A Stewart Platform-Based Manipulator: General Theory and Practical Construction," Int. J. Robotics Research, 1986, vol. 5, pp. 157-182.
Fishman et al., "Flouroscopically Assisted Cochlear Implantation," Otology & Neurotology, 2003, vol. 24, pp. 882-886.
Fitts, "The information capacity of the human motor system in controlling the amplitude of movement," J. Exp. Psychol., 1954, vol. 47, No. 6, p. 381-391.
Frangieh et al., "Histopathologic study of nine branch retinal vein occlusions," Arch Ophthalmol., 1982, vol. 100, pp. 1132-1140.
Fras et al., "New stiff-flop module construction idea for improved actuation and sensing," in 2015 IEEE International Conference on Robotics and Automation (ICRA), IEEE, 2015, pp. 2901-2906.
Freschi et al., "Technical review of the da Vinci surgical telemanipulator," Int. J. Med. Robot., 2013, 9: 396-406.
Fritzsche et al., "Resectoscope with an easy to use twist mechanism for improved handling," Current Directions in Biomedical Engineering, 2016, 2(1):379-382.
Gagarina et al., "Modeling and experimental analysis of a new bellow type actuators for active catheter end-effector," in Robot and Hu-man Interactive Communication, 2001. Proceedings. 10th IEEE International Workshop on, IEEE, 2001, pp. 612-617.
Gantz et al., "Preservation of hearing in cochlear implant surgery: advantages of combined electrical and acoustical speech processing," Laryngoscope, 2005, vol. 115, pp. 796-802.
Gaponov et al., Twisted string actuation systems: A study of the mathematical model and a comparison of twisted strings. IEEE/ASME Transactions on Mechatronics, 19(4), pp. 1331-1342.
Garbin et al., "Design of a Disposable Endoscope with Intrinsic Pneumatic Actuation," 2017, Hamlyn Symposium, London, Jun. 25-28.
Garbin et al., "Evaluation of a novel disposable upper endoscope for unsedated bedside (non-endoscopy unit based) assessment of the upper gastrointestinal (UGI) tract," DDW 2017, May 6-9, Gastrointestinal Endoscopy, 2017, vol. 85, No. 5S, Su1180.
Garbin et al., "Toward a low-cost soft robotic manipulator based on fluid-actuated bellows for gastric cancer screening," 2017, Hamlyn Symposium London, Jun. 25-28, 2017, 8 pages.
Gharib, "A new design for variable diameter orifice mechanism," in ASME 2012 International Mechanical Engineering Congress and Exposition. American Society of Mechanical Engineers, 2012, pp. 1551-1552.
Ghazvini, "Reducing the Inverse Kinematics of Manipulators to the Solution of a Generalized Eigenproblem," in Computational Kinematics: Kluwer Academic Publishers, 1993, pp. 15-26.
Goldman et al., "Compliant Motion Control for Multi-segment Continuum Robots With Actuation Force Sensing," IEEE Transaction on Robotics, 2014, vol. 30, No. 4, pp. 890-902.
Gong et al., "Four-arm robotic partial nephrectomy for complex renal cell carcinoma," World journal of urology, 2010, vol. 28, pp. 111-115.
Gosselin et al., "Singularity Analysis of Closed-Loop Kinematic Chains," IEEE Transactions on Robotics and Automation, 1990, vol. 6, pp. 281-290.
Gough et al., "Universal Tyre Test Machine," Proceedings, Ninth International Technical Congress F.I.S.I.T.A., 1962, pp. 117-137.
Grace, "Kinematic Design of an Opthalmic Surgery Robot and Feature Extracting Bilateral Manipulation," in Mechanical Engineering: Northwestern University, 1995, Dissertation, 95 pages.
Gravagne et al., "Large deflection dynamics and control for planar continuum robots," IEEE/ASME Trans. Mechatronics, 2003, vol. 8, No. 2, pp. 299-307.
Gstoettner et al., "Hearing preservation in cochlear implantation for electric acoustic stimulation," Acta Otolaryngol, 2004, vol. 124, pp. 348-352.

(56) References Cited

OTHER PUBLICATIONS

Guo et al., "Micro Active Guide Wire Catheter System—Characteristic Evaluation, Electrical Model and Operability Evaluation of Micro Active Catheter," IEEE International Conference on Robotics and Automation (ICRA'96), 1996, pp. 2226-2231.

Guo et al., "Micro Active Guide Wire Catheter System—Characteristic Evaluation, Electrical Model and Operability Evaluation of Micro Active Catheter," Sixth Int'l Symposium on Micro Machine and Human Science (MHS'95), 1995, pp. 131-136.

Guo et al., "Micro Active Guide Wire Catheter System," IEEE International Conference on Robotics and Automation, 1995, pp. 172-177.

Guo et al., "Micro Catheter System with Active Guide Wire—Structure, Experimental Results and Characteristic Evaluation of Active Guide Wire Catheter Using Icpf Actuator," Proc. 5th Int'l Symp. on Micro Machine and Human Science (MHS'94), 1994, pp. 191-197.

Gupta et al., "Current and evolving uses of optical coherence tomography in the genitourinary tract," Curr. Urol. Rep., 2015, 16:15, 7 pages.

Haber et al., "Novel robotic da Vinci instruments for laparoendoscopic single-site surgery," Urology, 2010, vol. 76, pp. 1279-1282.

Haga et al., "Small Diameter Active Catheter Using Shape Memory Alloys," Proc. of IEEE Micro Electro Mechanical Systems, 1998, pp. 419-424.

Hale, "Medical Applications of magnet Devices," IEEE Transactions on Magnetics, 1975, vol. 11, pp. 1405-1407.

Hannan et al., "Analysis and initial experiments for a novel elephant's trunk robot," IEEE/RSJ International Conference on Intelligent Robots and Systems (IROS 2000), 2000, pp. 330-337.

Hannan et al., "The 'elephant trunk' manipulator, design and implementation," proceedings of IEEE/ASME International conference on Advanced Intelligent Mechatronics, 2001, vol. 1, pp. 14-19.

Haritoglou et al., "Five-year follow-up of macular hole surgery with peeling of the internal limiting membrane: update of a prospective study," Retina, 2006, vol. 26(6), pp. 618-622.

Hassan et al., "Active-braid, a bioinspired continuum manipulator," IEEE Robotics and Automation Letters, 2017, vol. 2, No. 4, pp. 2104-2110.

Heimann et al., "Primary vitrectomy for rhegmatogenous retinal detachment: an analysis of 512 cases," Graefes Arch Clin Exp Ophthalmol., 2006, vol. 244, pp. 69-78.

Hendrick et al., "A multi-arm hand-held robotic system for transurethral laser Prostate surgery," in 2014 IEEE International Conference on Robotics and Automation (ICRA), 2014, pp. 2850-2855.

Henrich et al., "Quantification of Contrast Recognizability During Brilliant Blue G (BBG) and Indocyanine Green (ICG) Assisted Chromovitrectomy," Invest Ophthalmol Vis Sci., 2011, 52(7): 4345-4349.

Hirai et al., "Modeling of Deformable Thin Parts for their Manipulation," IEEE International Conference on Robotics and Automation, 1994, pp. 2955-2960.

Hirai et al., "Towards a Task Planning for Deformable object Manipulation-Formulation and Computation of Linear Object Deformation," IEEE International Conference on Robotics and Automation, 1995, pp. 80-85.

Hirose et al., "Coupled Tendon-Driven Multijoint Manipulator," IEEE Int. Conf. Robotics & Automation, 1991, pp. 1268-1275.

Hirose et al., "The Development of Soft Gripper for the Versatile Robot Hand," Mechanism and Machine Theory, 1987, vol. 13, pp. 351-359.

Hirose et al., "Tensor Actuated Elastic Manipulator," in Proceedings of the Sixth World Congress on Theory of Machines and Mechanisms, 1983, pp. 978-981.

Hockstein et al., "Robotic microlaryngeal surgery: a technical feasibility study using the daVinci surgical robot and an airway mannequin," The Laryngoscope, 2005, vol. 115, No. 5, pp. 780-785.

Hodac et al., "Decoupled macro/micro-manipulator for fast and precise assembly operations: design and experiments," in Proc. SPIE 3834, Microrobotics and Microassembly, 1999, pp. 122-130.

Hodges et al., "Conservation of residual hearing with cochlear implantation," Am J Otol, 1997, vol. 18, pp. 179-183.

Hongo et al., "NeuRobot: Telecontrolled Micromanipulator System for Minimally Invasive Microneurosurgery—Preliminary Results," Neurosurgery, 2002, vol. 51, pp. 985-988.

Hunt, "Structural Kinematics of In-Parallel-Actuated Robot arms," Journal of Mechanisms, Transmissions, and Automation in Design, 1983, vol. 105, pp. 705-712.

Husty, "An Algorithm for Solving the Direct Kinematics of General Stewart-Gough Platforms," Mechanism and Machine Theory, 1996, vol. 31, pp. 365-380.

Huttenbrink et al., "Movements of Cochlear Implant Electrodes Inside the Cochlea during Insertion: An X-ray Microscopy Study," Otology & Neurotology, 2002, vol. 23, pp. 187-191.

Hwang et al., "Combined arteriovenous sheathotomy and intraoperative intravitreal triamcinolone acetonide for branch retinal vein occlusion," Br J Ophthalmol, 2010, vol. 94, pp. 1483-1489.

Hyun-Soo Yoon et al., "A 4-DOF flexible continuum robot using a spring backbone," in Proc. IEEE Int. Conf. Mechatron. Autom., Changchun, China, 2009, pp. 1249-1254.

Ikuta et al., "Multi-degree of freedom hydraulic pressure driven safety active catheter," in Proc. IEEE Int. Conf. Robot. Autom., Orlando, FL, 2006, pp. 4161-4166.

Ikuta et al., "Remote Microsurgery System for Deep and Narrow Space Development of New Surgical Procedure and Micro-robotic Tool Sophisticated Medical Treatment and Cases," in Medical Image Computing and Computer-Assisted Intervention, Tokyo, Japan, 2002, pp. 163-172.

Immega et al., "The KSI Tentacle Manipulator," IEEE Int. Conf. on Robotics and Automation, 1995, pp. 3149-3154.

Innocenti, "Forward Kinematics in Polynomial Form of the General Stewart Platform," ASME J. of Mechanical Design, 2001, vol. 123, pp. 254-260.

International Search Report and Written Opinion for Application No. PCT/US2017/064271 dated Feb. 9, 2018 (7 pages).

International Search Report and Written Opinion for Application No. PCT/US2018/050948 dated Nov. 20, 2018 (8 pages).

Iqbal et al., "A guaranteed approach for kinematic analysis of continuum robot based catheter," in Robotics and Biomimetics (ROBIO), 2009 IEEE International Conference on, IEEE, 2009, pp. 1573-1578.

Ishiyama et al., "Magnetic micromachines for medical applications," Journal of Magnetism and Magnetic Materials, 2002, vol. 242-245, pp. 41-46.

Ivanescu et al., "A variable structure controller for a tentacle manipulator," in Proceedings of 1995 IEEE International Conference on Robotics and Automation, 1995, vol. 3, pp. 3155-3160.

Iyer et al., "An eye model for practicing vitreoretinal membrane peeling," Arch. Ophthalmol., 2006, vol. 124, No. 1, pp. 108-110.

James et al., "Preservation of residual hearing with cochlear implantation: how and why," Acta Otolaryngol, 2005, vol. 125, pp. 481-491.

Jayender et al., "Robot-assisted Active Catheter Insertion: Algorithms and Experiments," Int. J. Robot. Res., 2009, vol. 28, No. 9, pp. 1101-1117.

Jazayeri et al., "Distal digital replantation," Plast. Reconstr. Surg., 2013, vol. 132, No. 5, pp. 1207-1217.

Jensen et al., "Toward robot-assisted vascular microsurgery in the retina," Graefes Arch Clin Exp Ophthalmol, 1997, vol. 235, pp. 696-701.

Jerjes et al., "In vitro examination of suspicious oral lesions using optical coherence tomography.," Br. J. Oral Maxillofac. Surg., 2010, vol. 48, No. 1, pp. 18-25.

Jones et al., "A New Approach to Jacobian Formulation for a Class of Multi-Section Continuum Robots," in IEEE International Conference on Robotics and Automation, 2005, pp. 3268-3273.

Jones et al., "Practical Kinematics for Real-Time Implementation of Continuum Robots," IEEE Trans. Robot., 2006, vol. 22, No. 6, pp. 1087-1099.

Joos et al., "A miniature forward-imaging optical coherence tomography probe," in Proc. SPIE 8209, Ophthalmic Technologies XXII, 82090Z, 2012, p. 82090Z-82090Z-7.

(56) References Cited

OTHER PUBLICATIONS

Joos et al., "Miniature real-time intraoperative forward-imaging optical coherence tomography probe," Biomed. Opt. Express, 2013, vol. 4, No. 8, pp. 1342-1350.

Joos et al., "Preliminary Design and Evaluation of a B-Scan OCT-Guided Needle," Photonics, 2014, vol. 1, No. 3, pp. 260-266.

Kanazawa et al., "Current reconstructive techniques following head and neck cancer resection using microvascular surgery," Ann. Vasc. Dis., 2011, vol. 4, No. 3, pp. 189-195.

Kaouk et al., "Robotic assisted laparoscopic sural nerve grafting during radical prostatectomy: initial experience," J. Urol., 2003, vol. 170, No. 3, pp. 909-912.

Kapadia et al., "Empirical investigation of closed-loop control of extensible continuum manipulators," in 2014 IEEE/RSJ International Conference on Intelligent Robots and Systems, 2014, pp. 329-335.

Kapoor et al., "Constrained control for surgical assistant robots," in IEEE International Conference on Robotics and Automation, 2006, pp. 231-236.

Kapoor et al., "Telemanipulation of Snake-Like Robots for Minimally Invasive Surgery of the Upper Airway," in MICCAI 2006 workshop on medical robotics, Copenhagen, 2006.

Karger, "Architecture Singular Parallel Manipulators," in Advances in Robot Kinematics: Analysis and Control: Kluwer Academic Publishers, 1998, pp. 445-454.

Kaul et al., "da Vinci-assisted robotic partial nephrectomy: technique and results at a mean of 15 months of follow-up," European urology, 2007, vol. 51, discussion 191-2, pp. 186-191.

Kayalar et al., "Clinical applications of free arterialized venous flaps," J. Plast. Reconstr. Aesthet. Surg., 2014, vol. 67, No. 11, pp. 1548-1556.

Kazanzides et al., "An Integrated System for Cementless Hip Replacement," IEEE Engineering in Medicine and Biology, 1995, vol. 14, pp. 307-313.

Kelly, "Vitreous surgery for idiopathic macular holes: results of a pilot study," Arch Ophthalmol, 1991, vol. 109, pp. 654-659.

Kernt et al., "Indocyanine green increases light-induced oxidative stress, senescence, and matrix metalloproteinases I and 3 in human RPE cells," Acta Ophthalmol, 2012, 90: 571-579.

Ketten et al., "In vivo measures of cochlear length and insertion depth of Nucleus cochlear implant electrode arrays," Ann. Otol. Rhinol. Laryngol., 1998, vol. 107, pp. 1-17.

Kha et al., "Stiffness properties for Nucleus standard straight and contour electrode arrays," Medical Engineering & Physics, 2004, vol. 26, pp. 677-685.

Kiefer et al., "Conservation of low-frequency hearing in cochlear implantation," Acta Otolaryngol, 2004, vol. 124, pp. 272-280.

Kienzle et al., "Total Knee Replacement," IEEE Engineering in Medicine and Biology, 1995, vol. 14, pp. 301-306.

Kim et al., "A physically-based haptic rendering for telemanipulation with visual information: Macro and micro applications," in 2008 IEEE/RSJ International Conference on Intelligent Robots and Systems, 2008, pp. 3489-3494.

Kim et al., "Inchworm-like colonoscopic robot with hollow body and steering device," JSME International Journal Series C Mechanical Systems, Machine Elements and Manufacturing, 2006, vol. 49, No. 1, pp. 205-212.

Knight et al., "Computer-assisted, robot-enhanced open microsurgery in an animal model," J. Laparoendosc. Adv. Surg. Tech. A, 2005, vol. 15, No. 2, pp. 182-185.

Kutz et al., "Neuropsychological testing in the screening for cochlear implant candidacy," Laryngoscope, 2003, vol. 113, pp. 763-766.

Kwartowitz et al., "Toward image-guided robotic surgery: determining intrinsic accuracy of the da Vinci robot," Int. J. Comput. Assist. Radiol. Surg., 2006, vol. 1, No. 3, pp. 157-165.

Kwartowitz et al., "Update: Toward image-guided robotic surgery: determining the intrinsic accuracy of the daVinci-S robot," Int. J. Comput. Assist. Radio!. Surg., 2007, vol. 1, No. 5, pp. 301-304.

Laouri et al., "The burden of disease of retinal vein occlusion: review of the literature," Eye, 2011, 25: 981-988.

Lazard, "On the Representation of Rigid-Body Motions and Its Application to Generalized Platform Manipulators," Computational kinematics, 1993, pp. 175-181.

Lee et al., "Elimination-Based Solution Method for the Forward Kinematics of the General Stewart-Gough Platform," Computational Kinematics (CK2001), 2001, pp. 259-266.

Lee et al., "Human-guided surgical robot system for spinal fusion surgery: CoRASS," in 2008 IEEE International Conference on Robotics and Automation, ICRA 2008, May 19-May 23, 2008, Pasadena, CA, United States, 2008, pp. 3881-3887.

Lee et al., "Urgent bedside endoscopy for clinically significant upper gastrointestinal hemorrhage after admission to the intensive care unit," Intensive care medicine, 2003, 29(10): 1723-1728.

Leitner et al., "Computer-Assisted Knee Surgical Total Replacement," in Lecture Notes in Computer Science (LNCS) vol. 1205, J. Troccaz, E. Grimson, and R. Mosges, Eds.: Springer, 1997, 629-638.

Li et al., "Design and Study of a Novel Hyper-Redundant Manipulator," Robotica, 2003, vol. 21, pp. 505-509.

Li et al., "Spatial Motion Constraints in Medical Robot Using Virtual Fixtures Generated by Anatomy," in IEEE International Conference on Robotics & Automation, 2004, pp. 1270-1275.

Li et al., "A miniature B-scan forward-imaging OCT probe to guide real-time laser ablation," in Association for Research in Vision and Ophthalmology (ARVO) Annual Meeting, 2012.

Li et al., "Design of Continuous Backbone, Cable-Driven Robots," 2002, vol. 124, pp. 265-271.

Li et al., "Feasibility study on bonding quality inspection of microfluidic devices by optical coherence tomography," J. Biomed. Opt., 2011, 16(6): 066011, 9 pages.

Li et al., "Miniature forward-imaging B-scan optical coherence tomography probe to guide real-time laser ablation," Lasers Surg. Med., 2014, vol. 46, No. 3, pp. 193-202.

Lim et al., "Future of active catheters," Sensors and Actuators, 1996, vol. 56, pp. 113-121.

Lim et al., "Multi-link active catheter snake-like motion," Robotica, 1996, vol. 14, pp. 499-506.

Lipska et al., "Anastomotic leakage after lower gastrointestinal anastomosis: men are at a higher risk," Anz J. Surg., 2006, vol. 76, No. 7, pp. 579-585.

Liu et al., "Learning Insertion Task of a Flexible Beam by Virtual Agents," IEEE International Conference on Robotics and Automation, 2002, pp. 3290-3295.

Lohmeyer et al., "Prospective clinical study on digital nerve repair with collagen nerve conduits and review of literature," J. Reconstr. Microsurg., 2014, vol. 30, pp. 227-234.

Ma et al., "Architecture Singularities of Parallel Manipulators," IEEE International Conference on Robotics and Automation, 1991, pp. 1542-1547.

Maden et al., "A review of planar scissor structural mechanisms: geometric principles and design methods," Architectural Science Review, 2011, vol. 54, No. 3, pp. 246-257.

Mader et al., "Ocular war injuries of the Iraqi insurgency," Jan.-Sep. 2004. Ophthalmology, 2006, 113:97-104.

Maeda et al., "Active endoscope with SMA (Shape Memory Alloy) coil springs," in Proc. IEEE 9th Int. Workshop Microelectromech. Syst., San Diego, CA, 1996, pp. 290-295.

Maghooa et al., "Tendon and pressure actuation for a bio-inspired manipulator based on an antagonistic principle," in 2015 IEEE International Conference on Robotics and Automation (ICRA), IEEE, 2015, pp. 2556-2561.

Malik, "Human development report," United Nations Development Programme: UNDP Report, 2013, 216 pages.

Manolidis et al., "Do the genes that cause otosclerosis reduce susceptibility to otitis media?" Otol Neurotol, 2003, vol. 24, pp. 868-871.

Manolidis et al., "Use of reconstructed, nonorthogonal plane, high-resolution computed tomography of the temporal bone in the planning of temporal bone surgery," Orl J Otorhinolaryngol Relat Spec, 2003, vol. 65, pp. 71-75.

Manolidis et al., "Robotic insertion of cochlear implant electrodes to minimize cochlear trauma." 6th European Congress of Oto—Rhino—Laryngology, Head & Neck Surgery, Vienna, Austria, 2007.

(56) References Cited

OTHER PUBLICATIONS

Mason et al., "Sheathotomy to decompress branch retinal vein occlusion: a matched control study," Ophthalmology, 2004, vol. 111, pp. 540-545.

Matsumura et al., "Microvascular anastomosis at 30-50x magnifications (super-microvascular anastomosis) in neurosurgery," Surg. Neurol. Int., 2011, vol. 2, 6 pages.

Matsunaga et al., "Histopathologic evaluation of the internal limiting membrane surgically excised from eyes with diabetic maculopathy," Retina, 2005, vol. 25, pp. 311-316.

McIntosh et al., "Interventions for branch retinal vein occlusion: an evidence-based systematic review," Ophthalmology, 2007, vol. 114, pp. 835-854.

McMahan et al., "Field trials and testing of the octarm continuum manipulator," in Robotics and Automation, 2006. ICRA 2006. Proceedings 2006 IEEE International Conference on. IEEE, 2006, pp. 2336-2341.

Meeker et al., "Optimal Realization of Arbitrary Forces in a Magnetic Sterotaxis System," IEEE Transactions on Magnetics, 1996, vol. 32, pp. 320-328.

Merlet, "An Initiative for the Kinematic Study of Parallel Manipulators," Proceedings of the Workshop on Fundamental Issues and Future Research Directions for Parallel Mechanisms and Manipulators, 2002, 8 pages.

Merlet, "Kinematics is Not Dead!" IEEE International Conference on Robotics and Automation, 2000, pp. 1-6.

Merlet, "Parallel manipulators: state of the art and perspective," Journal of Robotics Society of Japan, 1992, vol. 10, pp. 57-62.

Merlet, "Parallel Robots: Open Problems," 9th International Symposium of Robotics Research, Snowbird, 1999, pp. 23-28.

Merlet, "Singular configurations of parallel manipulators and Grassmann geometry," in Geometry and Robotics, vol. LNCS 391, B. J-D. and J-P.Laumond, Eds., 1989, pp. 194-212.

Merlet, "Singular configurations of parallel manipulators and Grassmann geometry," Int. J. of Robotics Research, 1989, vol. 8, pp. 45-56.

Merzouki et al., "Compensation of friction and backlash effects in an electrical actuator," J. Syst. Cont. Eng., 2004, vol. 218, No. 2, 10 pages.

Mester et al., "Vitrectomy with aiteriovenous decompression and internal limiting membrane dissection in branch retinal vein occlusion," Retina, 2002, vol. 22, pp. 740-746.

Mikhail et al., "Robotic-assisted laparoscopic prostatectomy: first 100 patients with one year of follow-up.," Urology, 2006, vol. 68, No. 6, pp. 1275-1279.

Mineta, "Batch fabricated flat meandering shape memory alloy actuator for active catheter," Sensors and Actuators A, 2001, vol. 88, pp. 112-120.

Mochiyama et al., "Direct Kinematics of Manipulators with Hyper Degrees of Freedom and Fernet-Serret Formula," International Conference on Robotics and Automation, 1998, pp. 1653-1658.

Mochiyama et al., "Shape Correspondence between a Spatial Curve and a Manipulator with Hyper Degrees of Freedom," IEEE/RSJ International conference on Intelligent Robots and Systems (IROS'), 1998, pp. 161-166.

Mochiyama et al., "The Shape Jacobian of a Manipulator with Hyper Degrees of Freedom," IEEE International Conference on Robotics and Automation, 1999, pp. 2837-2842.

Mochiyama et al., "Shape Control of Manipulators with Hyper Degrees of Freedom," Int. J. Robot. Res., 1999, vol. 18, No. 6, pp. 584-600.

Moll et al., "Path Planning for Variable Resolution Minimal-Energy Curves of Constant Length," IEEE International Conference on Robotics and Automation, Barcelona, Spain, 2005, pp. 2130-2135.

Möller, "Gröbner Bases and Numerical Analysis," in Gröbner Bases and Applications, Lecture Note Series 251—London Mathematical Society, B. Buchberger and F. Winkler, Eds., 1998, pp. 159-178.

Montesi et al., "An SMA-base flexible active endoscope for minimal invasive surgery," Journal of Micromechanics and Microengineering, 1995, vol. 5, pp. 180-182.

Nagatsu et al., "Macro-micro bilateral control using Kalman filter based state observer for noise reduction and decoupling of modal space," in IECON 2013—39th Annual Conference of the IEEE Industrial Electronics Society, 2013, pp. 4192-4197.

Nakagaki et al., "Study of insertion Task of a Flexible Beam into a Hole," IEEE International Conference on Robotics and Automation, 1995, pp. 330-335.

Nakagaki et al., "Study of Insertion Task of a Flexible Wire into a Hole by Using Visual Tracking Observed by Stereo Vision," IEEE International Conference on Robotics and Automation, 1996, pp. 3209-3214.

Nakamura et al., "A robotic neurosurgery system with autofocusing motion control for mid-infrared laser ablation," in MICCAI'2006 workshop on medical robotics, Copenhagen, Denmark, 2006, pp. 108-115.

Nakamura et al., "Inverse Kinematic Solutions With Singularity Robustness for Robot Manipulator Control," J. Dyn. Syst. Meas. Control, 1986, vol. 108, No. 3, p. 163-171.

Nguyen et al., "A tendon-driven continuum robot with extensible sections," in Intelligent Robots and Systems (IROS), 2015 IEEE/RSJ International Conference on. IEEE, 2015, pp. 2130-2135.

NIDCD, "Presbycusis according to NIDCD," 2016, <https://www.nidcd.nih.gov/sites/default/files/Content%20Images/presbycusis.pdf>.

Nielsen et al., "Solving the Input/Output Problem for Planar Mechanisms," ASME J. of Mechanical Design, 1999, vol. 121, pp. 206-211.

Noh et al., "A continuum body force sensor designed for flexible surgical robotics devices," in 2014 36th Annual International Conference of the IEEE Engineering in Medicine and Biology Society, IEEE, 2014, pp. 3711-3714.

Noh et al., "A three-axial body force sensor for flexible manipulators," in 2014 IEEE International Conference on Robotics and Automation (ICRA), IEEE, 2014, pp. 6388-6393.

Nukherjee, "Design of holonomic loops for repeatability in redundant manipulators," in Proceedings of 1995 IEEE International Conference on Robotics and Automation, vol. 3, pp. 2785-2790.

O'Brien et al., "3d force control system design for a hydraulic parallel bellows continuum actuator," in Robotics and Automation, 2001. Proceedings 2001 ICRA. IEEE International Conference on, IEEE, vol. 3, 2001, pp. 2375-2380.

Obstein et al., "Sa1665 ultra low-cost endoscopy for gastric cancer screening in low resource settings," Gastrointestinal Endoscopy, 2014, vol. 79, No. 5, AB293.

Oghalai et al., "Neonatal hearing loss in the indigent," Laryngoscope, 2002, vol. 112, pp. 281-286.

Oh et al., "Long-term visual outcome of arteriovenous adventitial sheathotomy on branch retinal vein occlusion induced macular edema," Korean J Ophthalmol, 2008, vol. 22, pp. 1-5.

Okie, "Traumatic brain injury in the war zone," N Engl J Med, 2005, 352(20):2043-2047.

Olsson et al., "Friction Models and Friction Compensation," European Journal of Control, 1998, vol. 4, No. 3, pp. 176-195.

O'Malley et al., "Robotic Anterior and Midline Skull Base Surgery: Preclinical Investigations," Int. J. Radiation Oncology Biol. Phys., 2007, vol. 69, pp. 2125-2128.

Opremcak, "Surgical decompression of branch retinal vein occlusion via arteriovenous crossing sheathotomy: a prospective review of 15 cases," Retina, 1999, vol. 19, pp. 1-5.

Osterloh, "Surgical decompression of branch retinal vein occlusions," Arch Ophthalmol., 1988, vol. 106, pp. 1469-1471.

Osuka et al., "Development of Mobile Inspection Robot for Rescue Activities: MIORA," IEEE/RSJ International Conference on Intelligent Robots and Systems, 2003, pp. 3373-3377.

Ota et al., "A Novel Highly Articulated Robotic Surgical System for Epicardial Ablation," in 30th Annual International IEEE EMBS Conference, Vancouver, British Colombia, Canada, 2008, pp. 250-253.

Paljug et al., "The JPL Serpentine Robot: a 12 DOF System for Inspection," IEEE Int. Conf. on Robotics and Automation, 1995, pp. 3143-3148.

(56) References Cited

OTHER PUBLICATIONS

Pantuck et al., "A Novel Resectoscope for Transurethral Resection of Bladder Tumprs and the Prostate," The Journal of Urology, 2007, vol. 178, 2331-2336.
Park et al., "A multilink active catheter with polyimide-based integrated CMOS interface circuits," Journal of Micromechanical Systems, 1999, pp. 349-357.
Park et al., "Macular hole surgery with internal-limiting membrane peeling and intravitreous air," Ophthalmology, 1999, vol. 106(7), pp. 1392-1397.
Patel et al., "Evaluation of a novel flexible snake robot for endoluminal surgery," Surgical endoscopy, 2015, vol. 29, No. 11, pp. 3349-3355.
Patrick et al., "Characterization of mechanical properties of single electrodes and multi-electrodes," Annals of Otology, Rhinology and Laryngologyment, 1987, vol. 96, pp. 46-48.
Patronik et al., "Crawling on the heart: a mobile robotics device for minimally invasive cardiac interventions," in MICCAI 2004 (7th International Conference on Medical Image Computing and Computer-Assisted Intervention), 2004, pp. 9-16.
Peersman et al., "Prolonged operative time correlates with increased infection rate after total knee arthroplasty," HSS J., 2006, vol. 2, No. 1, pp. 70-72.
Peirs et al., "Design of an Advanced Tool Guiding System for Robotic Surgery," in 2003 IEEE International Conference on Robotics and Automation, 2003, pp. 2651-2656.
Phee et al., "Analysis and Development of Locomotion Devices for the Gastrointestinal Tract," IEEE Transactions on Biomedical Engineering, 2002, vol. 49, pp. 613-616.
Phelan et al., "Laparoscopic partial nephrectomy and minimally invasive nephron-sparing surgery," Current urology reports, 2003, vol. 4, pp. 13-20.
Phillips et al., "Closed globe macular injuries after blasts in combat," Retina, 2013, 33(2):371-379.
Pickens et al., "A Pilot Ex-Vivo Evaluation of a Telerobotic System for Transurethral Intervention and Surveillance," J. Endourol., 2015, 29(2): 231-234.
Piltan et al., "Design Gradient Descent Optimal Sliding Mode Control of Continuum Robots," IAES Int. J. Robot. Autom., 2012, vol. 1, No. 4, pp. 175-189.
Popov et al., "Towards variable stiffness control of antagonistic twisted string actuators," In Intelligent Robots and Systems (IROS 2014), 2014 IEEE/RSJ International Conference, 2014, pp. 2789-2794.
Porpiglia, "Editorial comments to da Vinci-assisted robotic partial nephrectomy: technique and results at a mean of 15 months of follow-up," European urology, 2007, vol. 51, p. 191.
Portman et al., "Rigid 6-DOF parallel platform for precision 3-D micromanipulation," Int. J. Mach. Tools Manuf., 2001, vol. 41, No. 9, pp. 1229-1250.
Prasad et al., "Surgical robotics: impact of motion scaling on task performance," J. Am. Coll. Surg., 2004, vol. 199, No. 6, pp. 863-868.
Pritts et al., "Design of an artificial muscle continuum robot," in Robotics and Automation, 2004. Proceedings. ICRA'04. 2004 IEEE International Conference on, vol. 5. IEEE, 2004, pp. 4742-4746.
Quiram et al., "Outcomes of vitrectomy with inferior retinectomy in patients with recurrent rhegmatogenous retinal detachments and proliferative vitreoretinopathy," Ophthalmology, 2006, 113:2041-2047.
Raghavan et al., "Solving Polynomial Systems for the Kinematic Analysis and Synthesis of Mechanisms and Robot Manipulators," ASME J. of Mechanical Design, 1995, vol. 117, pp. 71-79.
Raghavan, "The Stewart Platform of General Geometry Has 40 Configurations," ASME J. of Mechanical Design, 1993, vol. 115, pp. 277-282.
Rehak, "Branch retinal vein occlusion: pathogenesis, visual prognosis, and treatment modalities," Curr Eye Res, 2008, vol. 33, pp. 111-131.
Reynaerts et al., "Shape memory micro-actuation for a gastrointestinal intervention system," Sensors and Actuators, vol. 77, pp. 157-166, 1999.
Rhode, "Large Deflections of Cantilever Beam with Uniformly Distributed Load," Q. Appl. Math., 1953, vol. 11, pp. 337-338.
Roberts et al., "A comparison of two methods for choosing repeatable control strategies for kinematically redundant manipulators," in Proceedings 1992 IEEE International Conference on Robotics and Automation, 1992, pp. 514-519.
Rodanant et al., "Sheathotomy without separation of venule overlying arteriole at occlusion site in uncommon branch retinal vein occlusion," J Med Assoc Thai., 2005, vol. 88, pp. 143-150.
Rogers et al., "Robotic partial nephrectomy for renal hilar tumors: a multi-institutional analysis," The Journal of urology, 2008, vol. 180, discussion 2356, pp. 2353-2356.
Rogers et al., "Robotic partial nephrectomy: the real benefit," Current opinion in urology, 2011, vol. 21, pp. 60-64.
Rogers et al., "The prevalence of retinal vein occlusion: pooled data from population studies from the United States, Europe, Asia, and Australia," Ophthalmology, 2010, vol. 117, pp. 313-319.
Roland, "A model for cochlear implant electrode insertion and force evaluation: results with a new electrode design and insertion technique," The Laryngeoscope, 2005, vol. 115, pp. 1325-1339.
Rone et al., "Continuum Manipulator Statics Based on the Principle of Virtual Work," in vol. 4: Dynamics, Control and Uncertainty, Parts A and B, 2012, 8 pages.
Roth, "Computation in Kinematics," Computational Kinematics, 1993, pp. 3-14.
Roy et al., "Investigation of effects of dynamics on intrinsic wrench sensing in continuum robots," in Robotics and Automation (ICRA), 2016 IEEE International Conference on. IEEE, 2016, pp. 2052-2059.
Rucker et al., "Statics and Dynamics of Continuum Robots With General Tendon Routing and External Loading," IEEE Trans. Robot., 2011, vol. 27, No. 6, pp. 1033-1044.
Rul et al., "A Novel Tool Using SMA Actuator for cell puncturing," in SICE Annual Conference 2007, 2007, pp. 254-258.
Russo et al., "A Novel Robotic Platform for Laser Assisted Transurethral Surgery of the Prostate," IEEE Trans. Biomed. Eng., vol. 9294, No. c, pp. 1-12, 2014.
Safarik, "Editorial comments to da Vinci-assisted robotic partial nephrectomy: technique and results at a mean of 15 months of follow-up," European urology, 2007, vol. 51, p. 192.
Salisbury et al., "Preliminary design of a whole-arm manipulation system (WAMS)," in Proc. IEEE Int. Conf. Robot. Autom., Philadelphia, PA, 1988, pp. 254-260.
Sanchez et al., "New master arm for transurethral resection with a robot," Arch. Espanoles Urol., 2002, vol. 55, No. 10, pp. 1247-1250.
Saraf, "Robotic Assisted Microsurgery (RAMS): Application in Plastic Surgery," in Medical Robotics, V. Bozovic, Ed. 2008, pp. 364-376.
Sareh et al., "Bio-inspired tactile sensor sleeve for surgical soft manipulators," in 2014 IEEE International Conference on Robotics and Automation (ICRA), IEEE, 2014, pp. 1454-1459.
Schnider et al., "PADyC: a Synergetic Robot for Cardiac Puncturing," in IEEE International Conference on Robotics and Automation, San Francisco, CA, 2000, pp. 2883-2888.
Scholkopf et al., "New support vector algorithms," Neural Comput., 2000, vol. 12, No. 5, pp. 1207-1245.
Schriber, "Volvo Chooses Spine Robot for Spray Operations," in Robotics Today, 1984, pp. 28.
Schurzig et al., "A force sensing Automated Insertion Tool for cochlear electrode implantation," in IEEE International Conference on Robotics and Automation, 2010, pp. 3674-3679.
Scott et al., "A randomized trial comparing the efficacy and safety of intravitreal triamcinolone with standard care to treat vision loss associated with macular Edema secondary to branch retinal vein occlusion: the Standard Care vs Corticosteroid for Retinal Vein Occlusion (SCORE) study report 6," Arch Ophthalmol, 2009, vol. 127, pp. 1115-1128.
Sears et al., "Inverse Kinematics of Concentric Tube Steerable Needles," 2007, pp. 1887-1892.

(56) References Cited

OTHER PUBLICATIONS

Shah et al., "Adventitial sheathotomy for treatment of macular edema associated with branch retinal vein occlusion," Curr Opin Ophthalmol, 2000, vol. 11, pp. 171-174.
Shahinpoor et al., "Ionic Polymer-Metal Composites (IPMC) as biomimetic sensors and actuators," Proc. SPIE's 5th Int'l Symp. on Smart Structures and Materials, 1998, pp. 251-267.
Shamir et al., "Repeatability of redundant manipulators: mathematical solution of the problem," IEEE Trans. Automat. Contr., 1988, vol. 33, No. 11, pp. 1004-1009.
Shamir, "An overview on the global behavior of kinematically redundant robotic manipulators," in Eighteenth Convention of Electrical and Electronics Engineers in Israel, 1995, pp. 2.3.1/1-2.3.1/6.
Shamir, "Remarks on some dynamical problems of controlling redundant manipulators," IEEE Trans. Automat. Contr., 1990, vol. 35, No. 3, pp. 341-344.
Shen et al., "An intraocular OCT probe," in Association for Research in Vision and Ophthalmology (ARVO) Annual Meeting, 2011.
Shen et al., "Comparison of imaging a retinal mimicking phantom through air and vitreous substitutes with a 25-gauge B-scan OCT endoprobe versus an 18 mm telecentric OCT probe," in Association for Research in Vision and Ophthalmology (ARVO) Annual Meeting, 2014.
Shen et al., "Management of gastric cancer in Asia: Resource-stratified guidelines," The lancet oncology, 2013, vol. 14, No. 12, e535-e547.
Shiakolas et al., "On the Accuracy, Repeatability, and Degree of Influence of Kinematics Parameters for Industrial Robots," Int. J. Model. Simul., 2002, vol. 22, No. 3, 10 pages.
Shiva et al., "Tendon-based stiffening for a pneumatically actuated soft manipulator," IEEE Robotics and Automation Letters, 2016, vol. 1, No. 2, pp. 632-637.
Shoham et al., "Bone-Mounted Miniature Robot for Surgical Procedures: Concept and Clinical Applications," IEEE Transactions on Robotics and Automation, 2003, vol. 19, pp. 893-901.
Shoham et al., "Robot Construction for Surgery," First Israeli Symposium on Computer-Aided Surgery, Medical Robotics, and Medical Imaging (ISRACAS'98), Technion City, Haifa, Israel, 1998.
Simaan et al., "Remarks on Hidden Lines in Parallel Robots," 7th International Symposium on Advances in Robot Kinematics (ARK 2000), Piran-Portoroz, Slovenia, 2000.
Simaan et al., "Robot Construction for Surgical Applications," The 1st IFAC Conference on Mechatronic Systems, Darmstadt, Germany, 2000, pp. 553-558.
Simaan et al., "Stiffness Synthesis of a Variable Geometry Planar Robot," Advances in Robot Kinematics: Theory and Applications, 2002, pp. 463-472.
Slutsky, "The management of digital nerve injuries," J. Hand Surg. Am., 2014, vol. 39, pp. 1208-1215.
Smiddy et al., "Internal limiting membrane peeling in macular hole surgery," Ophthalmology, 2001, vol. 108(8), pp. 1471-1476.
Smiddy, "Economic Considerations of Macular Edema Therapies," Ophthalmology, 2011, pp. 1827-1833.
Soper et al., "Surface mosaics of the bladder reconstructed from endoscopic video for automated surveillance," IEEE Trans. Biomed. Eng., 2012, vol. 59, No. 6, pp. 1670-1680.
Stetter, "Multivariate Polynomial Equations as Matrix Eigenproblems," Contributions in Numerical Mathematics, World Scientific Series in Applicable Analysis (WSSIAA), 1993, pp. 355-371.
Stewart et al., "World cancer report 2014," World Health Organization, 2014, 630 pages.
Stewart, "A Platform With Six Degrees-of-Freedom," The Institution of Mechanical Engineers, Proceedings 1965-1966, 1965, 180(15): 371-386.
Stilli et al., "Shrinkable, stiffness-controllable soft manipulator based on a bio-inspired antagonistic actuation principle," in 2014 IEEE/RSJ International Conference on Intelligent Robots and Systems, IEEE, 2014, pp. 2476-2481.
Su et al., "Augmented Reality During Robot-assisted Laparoscopic Partial Nephrectomy: Toward Real-Time 3D-CT to Stereoscopic Video Registration," Urology, 2009, vol. 73, pp. 896-900.
Sung et al., "Robotic Laparoscopic Surgery: a Comparison of the Da Vinci and Zeus Systems," Urology, 2001, vol. 58, pp. 893-898.
Suthakorn et al., "A New Inverse Kinematics Algorithm for Binary Manipulators with Many Actuators," Advanced Robotics, 2001, vol. 15, pp. 225-244.
Suzumori et al., "A Miniature Inspection Robot Negotiating Pipes of Widely Varying Diameter," IEEE International Conference on Robotics and Automation, 2003, pp. 2735-2740.
Suzumori et al., "Applying a Flexible Microactuator to Robotic Mechanisms," EEE robotics and Automation Magazine, 1992, vol. I, pp. 21-27.
Suzumori et al., "Development of Flexible Microactuators and Its Applications to Robotic Mechanisms," IEEE International Conference on Robotics and Automation, 1991, pp. 1622-1627.
Suzumori et al., "Flexible Microactuator for Miniature Robots," IEEE International Conference on Robotics and Automation, 1991, pp. 204-209.
Takahashi et al., "The development of an in-pipe microrobot applying the motion of an earthworm," 5th International Symposium on Micro Machine and Human Science, 1994, pp. 35-40.
Tatlicioglu et al., "Dynamic Modelling for Planar Extensible Continuum Robot Manipulators," in Proc. IEEE Int. Conf. Robot. Autom., 2007, pp. 1357-1362.
Taylor et al., "An image-directed robotic system for precise Orthopedic surgery," IEEE Transactions on Robotics and Automation, 1994, vol. 10, pp. 261-275.
Thorne et al., "Chechlear Fluid Space Dimensions for Six Species Derived From Reconstructions of Three-Dimensional Magnetic Resonance Images," The Laryngeoscope, 1999, vol. 109, pp. 1661-1668.
Tonini et al., "Auditory steady-state response audiometry in profound SNHL: the impact of abnormal middle ear function," Ear Nose Throat J, 2005, vol. 84, pp. 282, 284-286, 288.
Trejos et al., "Port placement for endoscopic cardiac surgery based on robot dexterity optimization," Barcelona, Spain, 2005, pp. 912-917.
Trivedi et al., "Model-Based Shape Estimation for Soft Robotic Manipulators: The Planar Case," J. Mech. Robot., 2014, vol. 6, No. 2, pp. 021005-1-021005-11.
Tsai et al., "Solving the Kinematics of the Most General Six-and Five-Degrees-of-Freedom Manipulators by Continuation Methods," ASME Transactions on of Mechanisms, Transmissions, and Automation in Design, 1985, vol. 107, pp. 189-200.
Tsukagoshi et al., "Active hose: an artificial elephant's nose with maneuverability for rescue operation," in Proc. IEEE Int. Conf. Robot. Autom., Seoul, Korea, 2001, pp. 2454-2459.
Ueta et al., "Robot-assisted vitreoretinal surgery: development of a prototype and feasibility studies in an animal model," Ophthalmology, 2009, vol. 116, pp. 1538-1543.
Van Den Heuvel et al., "Robotic assistance in microvascular surgery," in Medical Robotics, V. Bozovic, Ed. 2008, pp. 471-480.
Wakahara et al., "A Computer Aided Manipulation System for a Multijoint Inspection Robot," Proceedings of the 32nd Conference on Remote System Technology, 1984, pp. 33-38.
Wakamatsu et al., "Modeling of Linear objects Considering Bend, Twist, and Extensional Deformation," IEEE International Conference on Robotics and Automation, 1995, pp. 433-438.
Wakamatsu et al., "Static Analysis of Deformable Object Grasping Based on Bounded Force Closure," IEEE International Conference on Robotics and Automation, 1996, pp. 3324-3329.
Wakamatsu et al., "Static Modeling of Deformation Based on Differential Geometry," International Journal of Robotics Research, 2004, vol. 23, pp. 293-311.
Walker et al., "A Novel "Elephant's Trunk" Robot," Proceedings of the 1999 IEEE/ASME International Conference on Advanced Intelligent Mechatronics, 1999, pp. 410-415.
Walker et al., "Some Issues in Creating 'Invertebrate' Robots," In the Proceedings of the International Symposium on Adaptive Motion of Animals and Machines, Montreal, Canada, 2000, 6 pages.

(56) References Cited

OTHER PUBLICATIONS

Wampler et al., "Numerical Continuation Methods for Solving Polynomial Systems Arising in Kinematics," ASME Journal of Mechanical Design, 1990, vol. 112, pp. 59-68.
Wampler et al., "Manipulator Inverse Kinematic Solutions Based on Vector Formulations and Damped Least-Squares Methods," IEEE Trans. Syst. Man. Cybern., 1986, vol. 16, No. 1, pp. 93-101.
Wampler, "Solving the Kinematics of Planar Mechanisms by Dixon Determinant and a Complex-Plane Formulation," ASME J. of Mechanical Design, 2001, vol. 123, pp. 382-387.
Wang et al., "Conceptual design and dimensional synthesis of 'MicroHand," Mechanism and Machine Theory, 2008, vol. 43, No. 9, pp. 1186-1197.
Wang et al., "Investigation of Error Propagation in Multi-Backbone Continuum Robots," in Advances in Robot Kinematics, 2014, pp. 385-394.
Wardrop et al., "A temporal bone study of insertion trauma and intracochlear position of cochlear implant electrodes I: comparison of Nucleus banded and Nucleus Contour electrodes," Hearing Research, 2005, vol. 203, pp. 54-67.
Wardrop et al., "A temporal bone study of insertion trauma and intracochlear position of cochlear implant electrodes II: comparison of spiral clariontrade mark and HiFocus Iltrade mark electrodes banded and Nucleus Contour electrodes," Hearing Research, 2005, vol. 203, pp. 68-79.
Watson et al., "In vivo time-serial multi-modality optical imaging in a mouse model of ovarian tumorigenesis," Cancer Biol. Ther., 2014, vol. 15, No. 1, pp. 42-60.
Weichel et al., "Chorioretinectomy for perforating or severe intraocular foreign body injuries," Graefes Arch Clin Exp Ophthalmol., 2010, 248(3):319-330.
Weichel et al., "Traumatic macular holes secondary to combat ocular trauma," Retina, 2009, 29(3):349-54.
Widran, "Video transurethral resection using controlled continuous flow resectoscope," Urology, 1988, 31(5):382-6.
Williams, "Macular holes: the latest in current management," Retina, 2006, vol. 26(6 Suppl), pp. S9-S12.
Wolf et al., "A Mobile Hyper Redundant Mechanism for Search and Rescue Tasks," IEEE/RSJ International Conference on Intelligent Robots and Systems, 2003, pp. 2889-2895.
Wolf et al., "MBARS: Mini bone attached robotic system for joint arthroplasty," Pisa, Italy, 2006, pp. 1053-1058.
Wurdemann et al., "Embedded electro-conductive yarn for shape sensing of soft robotic manipulators," in 2015 37th Annual International Conference of the IEEE Engineering in Medicine and Biology Society (EMBC), IEEE, 2015, pp. 8026-8029.
Yamamoto et al., "Vitrectomy with or without arteriovenous adventitial sheathotomy for macular edema associated with branch retinal vein occlusion," Am J Ophthalmol, 2004, vol. 138, pp. 907-914.
Yamashita et al., "Handheld Laparoscopic Forceps manipulator Using Multi-slider Linkage Mechanisms," in MICCAI 2004 (7th International Conference on Medical Image Computing and Computer-Assisted Intervention), 2004, pp. 121-128.
Yoo et al., "Three-Dimensional Modeling and Visualization of the Cochlea on the internet," IEEE Transactions on Information Technology in Biomedicine, 2000, vol. 4, pp. 144-151.
Yoon et al., "A 4-dof flexible continuum robot using a spring backbone," in 2009 International Conference on Mechatronics and Automation, Aug. 2009, pp. 1249-1254.
Yoon et al., "Development of an Automated Steering Mechanism for Bladder Urothelium Surveillance," J. Med. Device., 2009, vol. 3, No. 1, p. 011004-1-011004-9.
Yu et al., "Evaluation of microsurgical tasks with OCT-guided and/or robot-assisted ophthalmic forceps," Biomed. Opt. Express, 2015, vol. 6, No. 2, p. 457-472.
Yun et al., "A novel design and analysis of a 3-DOF parallel manipulator for micro/nano manipulation," in 2008 IEEE Workshop on Advanced robotics and Its Social Impacts, 2008, pp. 1-6.
Zanganeh et al., "The inverse kinematics of hyper-redundant manipulators using splines," Proc. 1995 IEEE Int. Conf. Robot. Autom., 1995, vol. 3, pp. 2797-2802.
Zghal et al., "Efficient gradient projection optimization for manipulators with multiple degrees of redundancy," in Robotics and Automation, 1990. Proceedings., 1990 IEEE International Conference on. IEEE, 1990, pp. 1006-1011.
Zhang, "Design of Underactuated Steerable Electrode Arrays for Optimal Insertions," J. Mech. Robot., vol. 5, No. 1, p. 011008, Jan. 2013.
Zhang, "Flexible camera calibration by viewing a plane from unknown orientations," Proc. Seventh IEEE Int. Conf. Comput. Vis., vol. 1, 1999, 8 pages.
Zheng et al., "Use of a distal ulnar artery perforator-based bilobed free flap for repairing complex digital defects," J. Hand Surg. Am., 2014, vol. 39, No. 11, pp. 2235-2242.
Zheng et al., Strategies for Automatic Assembly of Deformable Objects, IEEE International Conference on Robotics and Automation, 1991, pp. 2598-2603.
Zlatanov et al., "A Unifying Framework for Classification and Interpretation of Mechanism Singularities," Asme J. of Mechanical Design, 1995, vol. 117, pp. 566-572.
Zlatanov et al., "Mechanical Design and Kinematic Analysis of a Three-Legged Six Degree-of-Freedom Parallel Manipulator," Robotics, Spatial Mechanisms, and Mechanical Systems DE, 1992, vol. 45, pp. 529-536.

\* cited by examiner

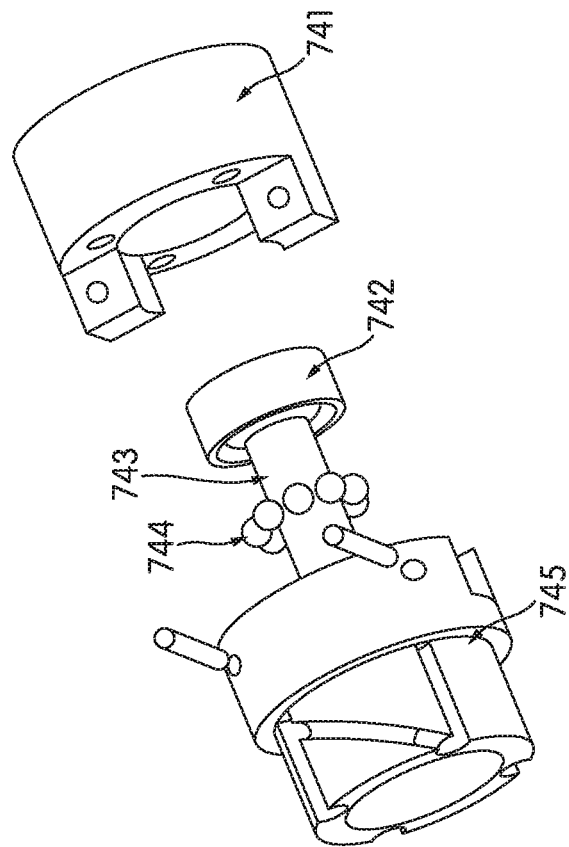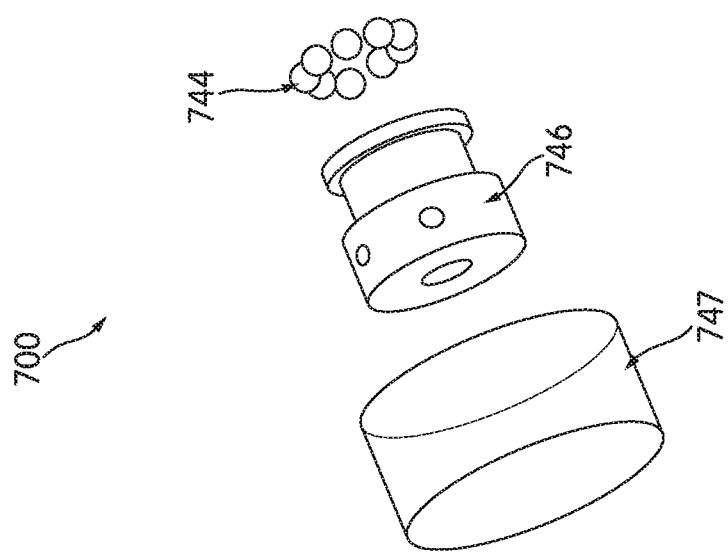
FIG. 7

DEXTEROUS WRISTS

RELATED APPLICATIONS

This application is a continuation of U.S. application Ser. No. 14/391,659, filed on Oct. 9, 2014, which is a national-stage entry of International Application No. PCT/US13/37336, filed Apr. 19, 2013, which claims priority to U.S. Provisional Application No. 61/636,001, filed on Apr. 20, 2012 and titled "DEXTEROUS WRISTS FOR SURGICAL INTERVENTION," the entire contents of all of which are incorporated herein by reference.

STATEMENT REGARDING FEDERALLY SPONSORED RESEARCH OR DEVELOPMENT

This invention was made with government support under grant 7R21EB007779-04 awarded by National Institutes of Health. The government has certain rights in the invention.

FIELD OF THE INVENTION

The present invention relates to dexterous gripping devices and surgical wrists. In particular, the invention relates to gripper assemblies with integrated axial rotation capabilities, selective detachability, and roll-yaw-pitch wrist action for use with robotic systems during minimally invasive surgical procedures.

SUMMARY

In one embodiment, the invention provides a continuum robot including a plurality of controllably bending continuum robot segments, a gripper, and a wrist. The continuum robot has tubular shafts (backbones) that actuate its segments to cause it to bend and also provide an actuation pathway for the gripper and the wrist. The gripper is selectively connectable to the distal end of the continuum robot (hereafter referred to as the end disk). A rotatable wrist connects the gripper to the end disk. The rotatable wrist includes a hub that is selectively connectable to the end disk. A wrist capstan is rotatably connected to the wrist hub and non-rotatably connected to the gripper base. A flexible wire rope enters the wrist hub through one tubular shaft (backbone), wraps around the wrist capstan and then returns through a second tubular shaft (backbone) of the continuum robot. This wire rope makes a closed loop distally connected to the wrist capstan and proximally connected to an actuation unit with a linear actuator and a tensioning idler pulley. Linear movement of the actuator causes linear movement of the flexible wire loop through the shafts of the continuum robot and thus causes rotation of the wrist capstan due to friction between the flexible wire loop and the wrist capstan.

In some embodiments, the wrist capstan includes a grooved surface and the flexible wire loop includes a spherical feature that meshes inside a matching grooved surface in the wrist capstan. In some such embodiments, the wire does not make a full turn around the capstan and torque transmission to the capstan relies on the positive lock between the spherical feature and the capstan rather than on friction between the wire rope and the capstan.

In some embodiments the wire rope is routed on idler pulleys in the wrist hub. The wire enters the wrist hub through one continuum robot shaft, bends on the circumference of a first idler pulley tangentially oriented to the wrist capstan, wraps fully or partially around the capstan, and returns on a second idler pulley in a similar manner into a second continuum robot shaft (backbone).

In some embodiments the idler pulleys are replaced by curved surfaces in the wrist hub in order to reduce size and cost. The wire rope then slides on these curved surfaces and wraps around the capstan. The curved surfaces may be treated with friction reducing treatments such as PTFE coatings or hard anodize treatment. The curved surface geometry is uniquely determined such that the first curved surface where the wire rope enters the wrist hub is placed at a height difference compared to the second curved surface where the wire rope exits the wrist hub. This axial height difference is determined by the pitch of the helical path of the wire rope winding around the capstan.

In some embodiments, the wrist hub includes a first helical circumferential groove and a second helical circumferential groove in the wrist hub. These grooves replace the function of the idler pulleys and allow transmission of the wire rope from the entry point of the wrist hub along the first helical path to a point of tangency to the wrist capstan and then returning to the second helical groove to the exit shaft in the continuum robot In some embodiments the wrist capstan is made of two parts comprising of a capstan shaft and a capstan ring. The capstan ring is attached to the capstan shaft in a manner that allows transmission of torque but does not allow transmission of axial motion. Such embodiment may include a spline shaft. In this design the capstan is allowed to move axially to conform with the movement of the helically wound wire rope loop.

In some embodiments the wrist base (hub) is attached to the end disk of the continuum robot through a revolute articulated joint (herein called pitch axis). Actuation of the wrist is achieved through a wire rope loop that passes through two backbones (shafts) of the continuum robot while bending of the pitch axis is achieved via a push-pull superelastic NiTi wire that passes through a third shaft of the continuum robot or via a wire rope loop that passes through two opposing shafts of the continuum robot.

In some embodiments the wrist base (hub) is attached to the end disk of the continuum robot through a universal (Cardan) articulated joint that provides bending in the yaw and pitch axes. Actuation of the wrist (roll axis) is achieved through a wire rope loop that passes through two backbones (shafts) of the continuum robot while bending of the pitch axis is achieved via a push-pull superelastic NiTi wire that passes through a third shaft of the continuum robot. Similarly, bending of the yaw axis is achieved via a push-pull superelastic NiTi wire that passes through a third shaft of the continuum robot.

Other aspects of the invention will become apparent by consideration of the detailed description and accompanying drawings.

BRIEF DESCRIPTION OF THE DRAWINGS

FIG. 7 is an exploded with of a rotatable gripper wrist according to a fourth embodiment.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Some surgical tools, such as described in U.S. Pub. No. 2011/0230894, which is incorporated herein by reference, include continuum robots with gripping tools connected to the distal end of the continuum robot. A continuum robot is a snake-like robot with a plurality of segments. The segments are controlled independently to adjust the shape and position of the continuum robot. Although some of these tools include articulated wrists for adjusting the position of the gripper, the existing tools are incapable of producing instrument roll about the gripper axis. This limits implementation of these devices for highly precise manipulations such as micro-surgery since very exact coordinated motion of several degrees of freedom is required.

Figure 1:
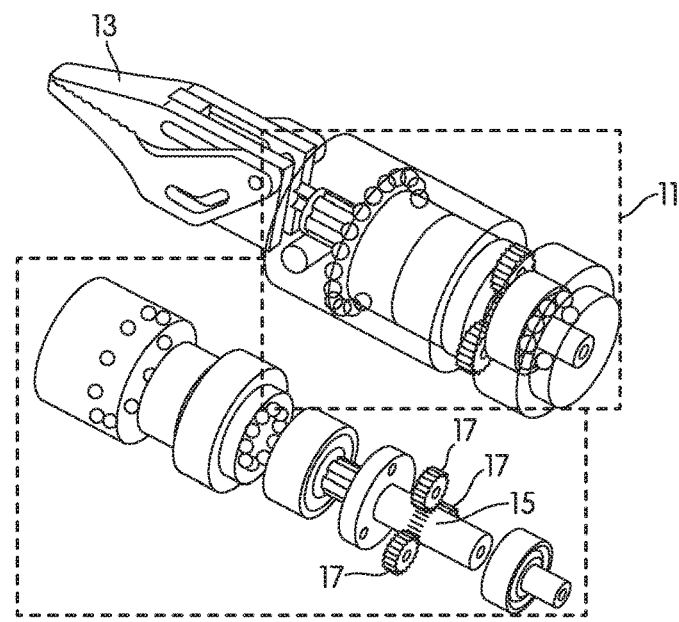
FIG. 1 is an exploded view of a rotatable gripper wrist according to one embodiment.

FIG. 1 illustrates a first example of an articulated wrist 11 that is capable of rotating the gripper 13 relative to the shaft (or plurality of segments) of a continuum robot or other device. The example of FIG. 1 is achieved using microplanetary gears. The sun gear 15 is actuated through a miniature torsional shaft and the planetary gears 17 amplify this torque and rotate the wrist about its axis.

Figure 2:
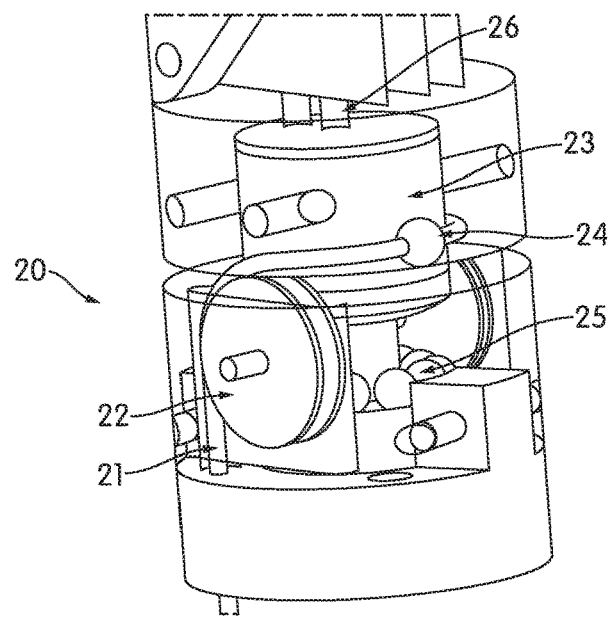
FIG. 2 is a view of a rotatable gripper wrist according to another embodiment.

FIG. 2 shows a different construction of a wrist assembly 20 that uses a miniature pulley with wire actuation to achieve rotation of the gripper. As illustrated, the ends of a wire loop 21 each pass across a pulley 22 extending into the shaft of the continuum robot. The wire loop is then positioned around a textured or grooved capstan assembly 23. As either end of the flexible wire loop 21 is inserted and retracted from the shaft of the continuum robot, the friction between the wire loop 21 and the capstan assembly 23 causes the capstan assembly to rotate relative to the shaft of the continuum robot. This rotation also causes the gripper to rotate. The ends of the wire loop extend through tubular structures in the shaft of the continuum robot called secondary backbones. The wire loop in the example of FIG. 2 includes a positive-locking, spherical shaped terminal 24 that is crimped on the flexible wire. The terminal 24 causes increased frictions between the flexible wire 21 and the capstan 23. The flexible wire in this example is a NiTi wire.

A plurality of ball bearings 25 are incorporated into the wrist assembly 200 to provide for smooth rotation of the capstan assembly 23 and, as a result, the gripper. The gripper is operated by a wire-based mechanism that extends through a channel 26 in the center of the capstan 23.

Figure 3:
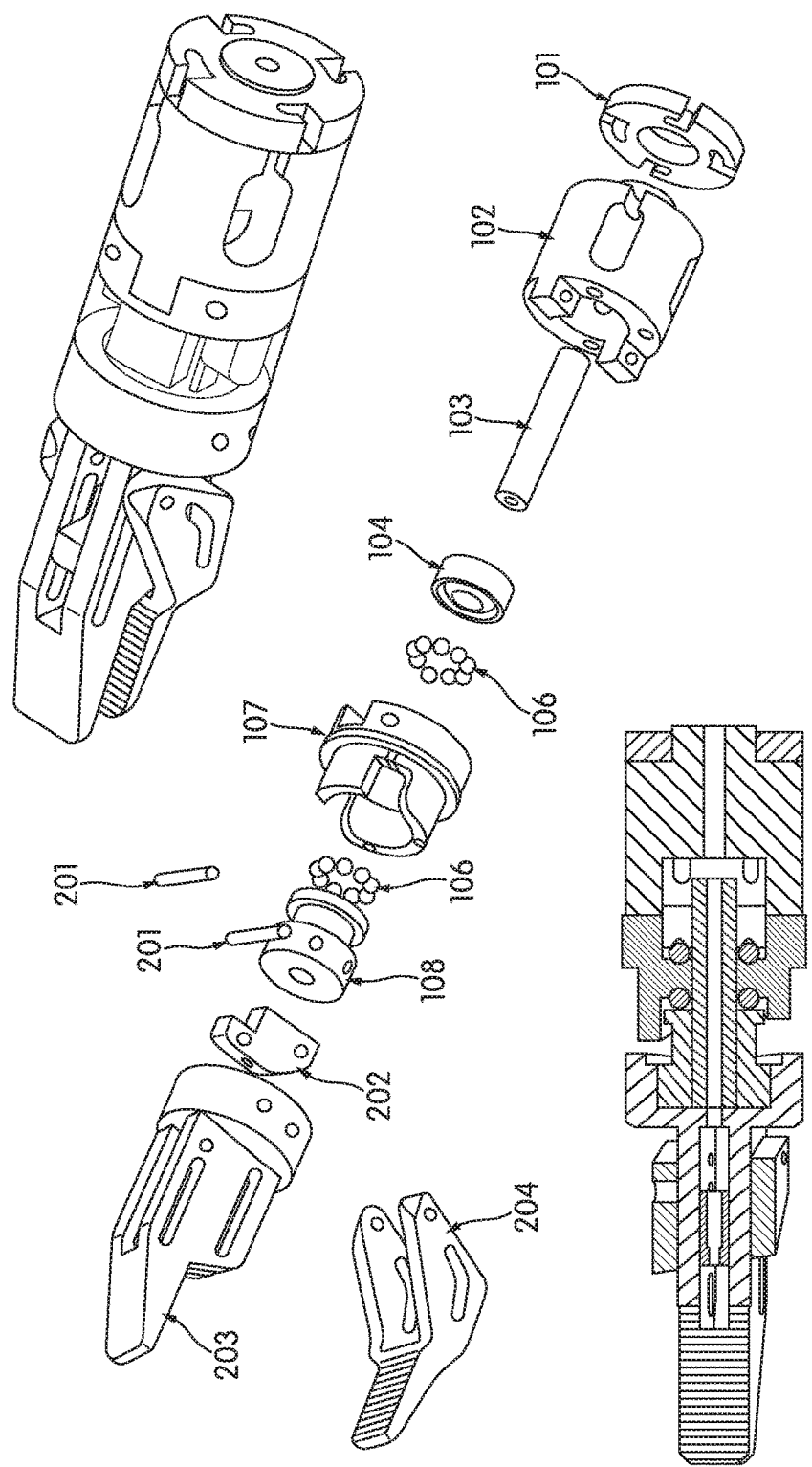
FIG. 3 is a exploded, perspective, and cross-sectional view of a rotatable gripper wrist according to a third embodiment.

FIG. 3 illustrates another example of a rotating wrist assembly. This assembly has two main sub-assemblies: the wrist and the gripper. The wrist base 102 allows the wrist and gripper to be selectively detached from the shaft (e.g., the snake arm) of the continuum robot and also serves as the end disk of a multi-backbone continuum snake robot. The lock nut 101 serves as a means of locking the wrist assembly to the secondary backbones of the snake arm. The hollow screw shaft 103 is threaded into the wrist capstan 108 and is glued to it or attached by press-fit. This screw shaft serves as the shaft hub locking the rotatable wrist capstan 108 to the wrist hub 107. Once the capstan 108 and the screw shaft 103 are connected they are inserted into a bearing made of the wrist capstan 108, the bearing balls 106, the wrist hub 107, and then locked by the lower bearing brace/lock nut 104. The wrist hub 107 is coupled to the wrist base 102 using shear pins.

The gripper includes a fixed jaw 203, a moving jaw 204, a sliding block 202, and a guiding pin. The gripper attaches to the rotating wrist capstan 108 using shear pins 201. Actuation of the gripper is achieved using a superelastic NiTi wire that pushes the sliding block 202, which in turn rotates the moving jaw using a shear pin that passes in the slot openings in the fixed and moving jaws.

The example of FIG. 3 differs from the example of FIG. 2 in that the pulleys are replaced by a wrist hub 107 with sliding surfaces to guide the flexible wire. Also, the example of FIG. 3 eliminates the positive locking terminal. As such, the flexible wire loop can be extended and retracted further linearly through the shaft of the continuum robot and the rotation of the wrist is not limited by a physical structure on the wire. Another difference is that the design in FIG. 3 allows detaching the wrist from the backbones of the snake segment. The end disk of the snake segment, which serves as the wrist hub 102 includes a series of linear grooves allowing for the side insertion of the NiTi backbones of the snake robot. The backbones have enlarged features at their tip that match the grooves in 102. A rotation of lock disk 101 selectively locks the backbones into the wrist hub 102. This selective locking functionality allows for easy replacement of wrist modules.

Figure 4A:
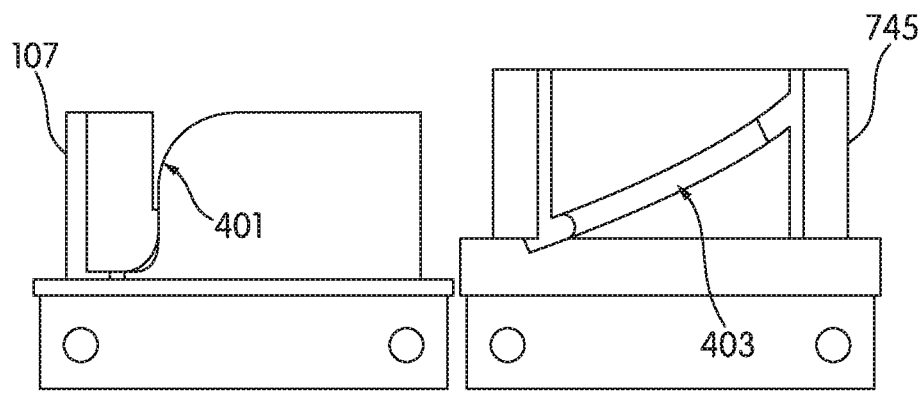
FIGS. 4A and 4B are detailed views of two examples of wrist hub components used with a rotatable gripper wrist.
Figure 4B:
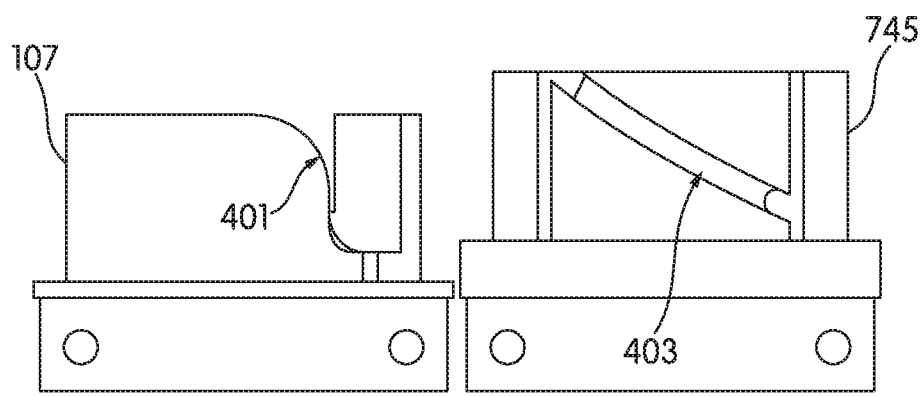

FIG. 4A illustrates the wrist hub 107 in further detail. The wrist hub 107 includes an extrusion 401 that guides the flexible wire and pushes it against the surface of the rotating capstan 108. FIG. 4B shows the wrist hub 107 from a different perspective.

Figure 5:
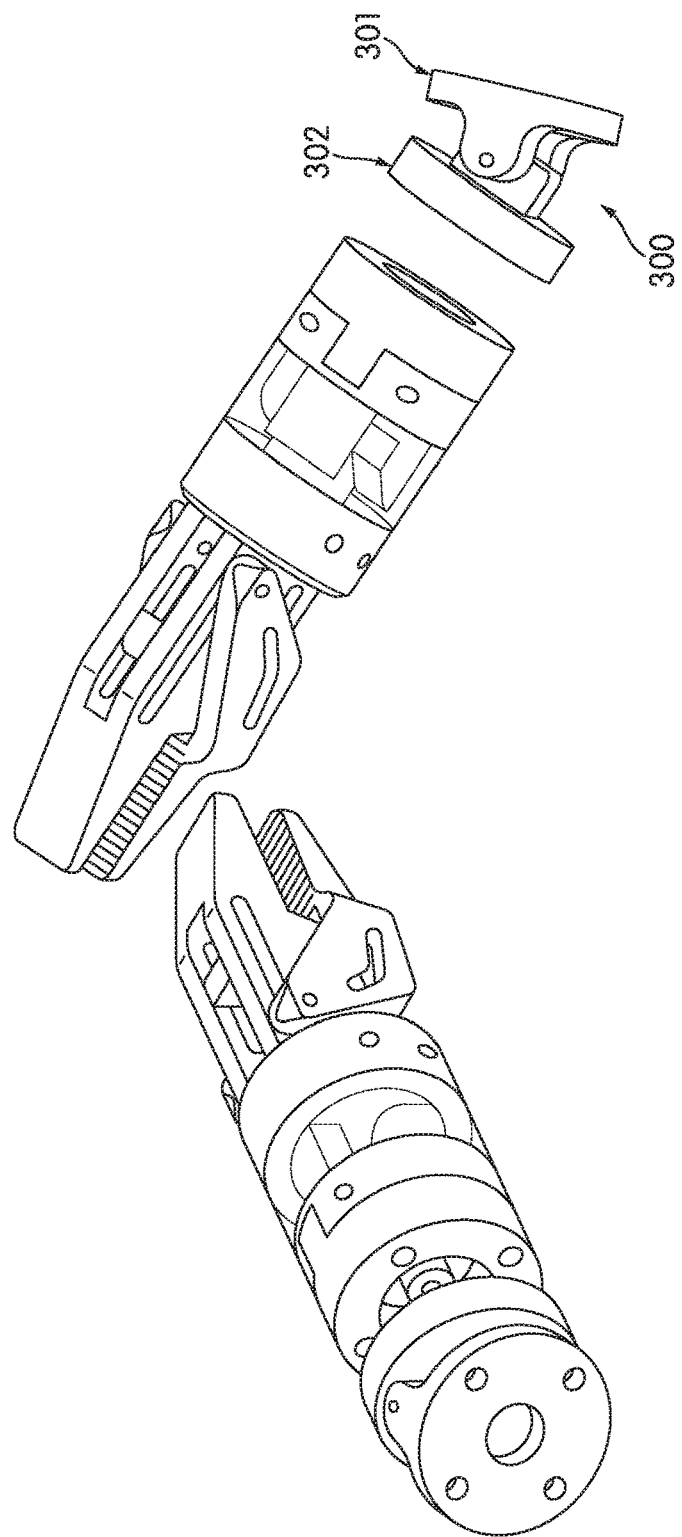
FIG. 5 is a perspective view of a wrist and gripper assembly with a pivot (pitch) joint.

FIG. 5 illustrates a pivot joint 300 that can be included to provide an additional degree of freedom to the rotatable gripper of FIG. 3. The added capability is achieved using a revolute joint assembly including a base 301 and an output link 302 pivotably connected via a pin. There are at least four holes through the base link that provide access for superelastic NiTi wires that control the rotatable gripper assembly. In one example, two adjacent holes are used to pass either end of the flexible wire loop used to actuate the rotatable wrist and the other two holes are used to actuate the revolute joint using push-pull actuation through a wire rope connected to the output link 302. In another embodiment, the revolute joint is actuated through superelastic NiTi tubes connected to the output link 302 and passing through guide tubes in the base 301 and the wrist is actuated through wire ropes that pass through the NiTi tubes of the revolute joint.

Figure 6:
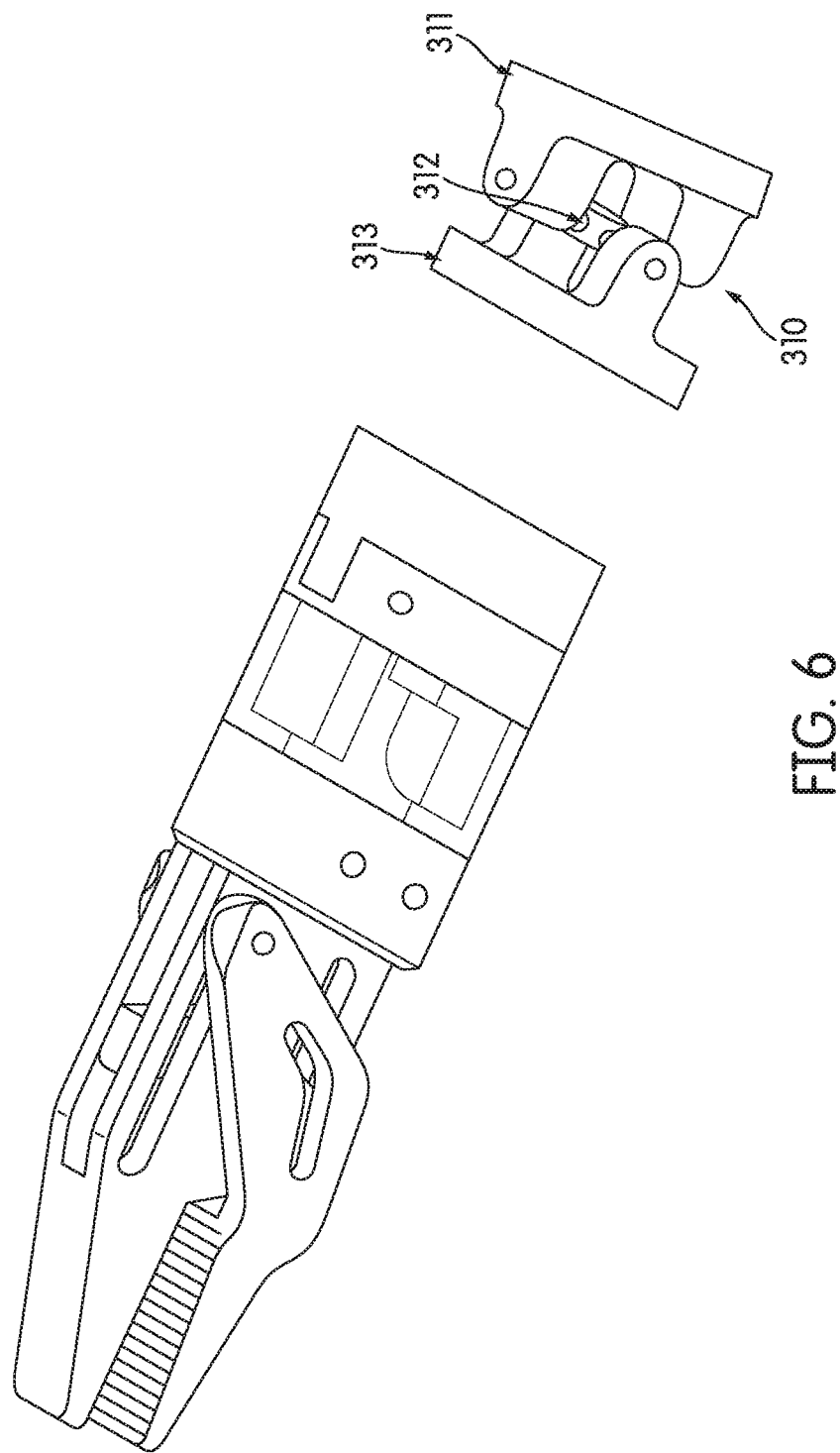
FIG. 6 is a perspective view of a wrist and gripper assembly with a gimbal (yaw and pitch) joint.

FIG. 6 illustrates an alternative joint assembly 310 for connecting the rotatable gripper to the shaft of the continuum robot. This example provides yet another degree of freedom (both yaw and pitch) in addition to the rotating capabilities. The added degree of freedom is achieved using a Cardan (Hooke) joint assembly. The joint assembly includes a base 311, a gimbal 312, and an output link 313. The gimbal is connected to the base and output links via pins. The base link again has at least four holes. In one example, two opposing holes are used to pass the actuation wires of the yaw degree of freedom while the other two holes are used to pass actuation wires of the pitch direction. The wrist actuation in a design using only four holes in the base 311 would require the use of a rotation tube and a gripper as illustrated in FIG. 1. In another embodiment, the base 311 has at least six holes and an additional center hole for actuating the gripper. Two holes are used to pass wires for actuating the pitch axis, two for actuating the yaw, and two to actuate the rotation of the gripper. In such constructions, a hole must also be provided through the center of gimbal 312 to allow the mechanism for actuating the gripper to pass through the joint 310. In some other constructions, gimbal 312 is replaced with a binary link having two axially offset pivots that are mutually perpendicular.

FIG. 7 illustrates another alternative rotatable wrist 700 for a gripper assembly. The wrist includes a snake end disk 741, a bearing nut 742, a vented screw 743, bearing balls 744, a wrist hub 745, a capstan 746, and a cover ring 747. When connected to the capstan assembly 746, the bearing nut 742 supports the bottom set of bearing balls 744 and locks the entire wrist structure around the wrist hub 745. The capstan 746 has locating pins for mounting the gripper jaw.

FIGS. 4A and 4B further illustrate the differences between the wrist hub 107 of the example of FIG. 3 and the wrist hub B45 of the example of FIG. 7. Wrist hub 107 includes two smooth extrusions 401 to allow routing of the wire rope loop that is used to control the rotation of the capstan and, thereby, the gripper. Wrist hub 745 includes a groove 403 that routes the wire rope to the correct position to wrap around the capstan 746. As the wire rope is inserted or retracted from the shaft of the continuum robot to control the rotation of the wrist, the wire rope move linearly through the grooves of the wrist hub 745.

Figure 8C:
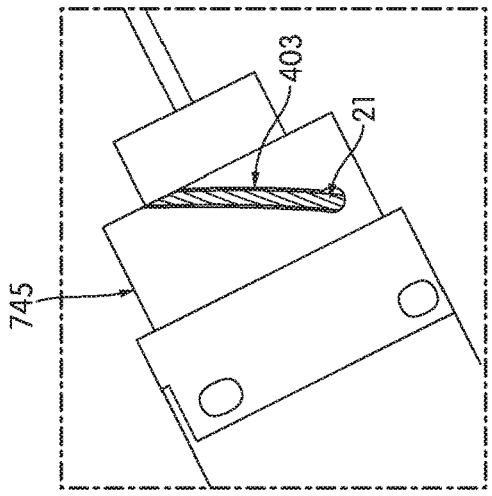
FIG. 8C is a side view of the assembled rotatable gripper wrist of FIG. 7 fitted with the flexible control wire.
Figure 8B:
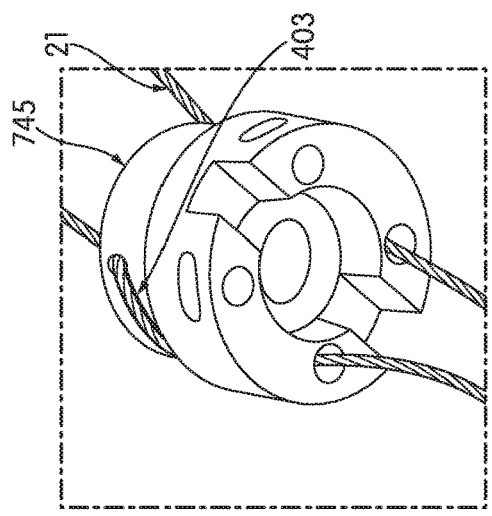
FIG. 8B is a perspective view of the bottom of the wrist hub of FIG. 8A.
Figure 8A:
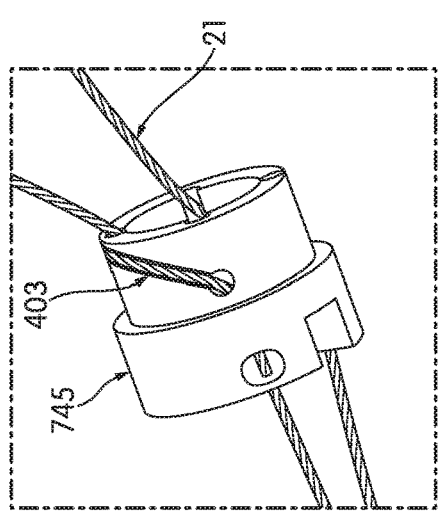
FIG. 8A is a side view of the wrist hub component of the rotatable gripper wrist of FIG. 7 fitted with a flexible control wire.

FIGS. 8A, 8B, and 8C show various components of the wrist assembly of FIG. 7 fitted with a flexible wire loop. FIG. 8A shows the wrist hub 745 from the side and illustrates the ends of the wire loop running through the grooves 403 of the wrist hub 745 and extending out of the bottom of the wrist hub 745. FIG. 8B shows the same assembly from the bottom. In FIG. 8C, the entire rotatable wrist assembly is assembled and attached to the distal end of a continuum robot. The wire loop is visible in the groove 403 of the wrist hub B75 in FIG. 8C.

Thus, the invention provides, among other things, a rotatable wrist assembly for an articulable gripper tool. Various features and advantages of the invention are set forth in the following claims.

What is claimed is:

1. A rotatable wrist comprising:
   a wrist hub including a first groove positioned at an angle relative to a rotational axis of the rotatable wrist;
   a wrist capstan rotatably connected to the wrist hub; and
   a flexible wire extending through the wrist hub and partially contacting the wrist capstan,
   wherein the flexible wire is partially positioned within the first groove of the wrist hub such that the first groove guides linear movement of the flexible wire, and wherein the linear movement of the flexible wire causes rotation of the wrist capstan due to friction between the flexible wire and the wrist capstan.

2. The rotatable wrist of claim 1, wherein the wrist hub further includes a second groove positioned at an angle relative to the rotational axis of the rotatable wrist, and wherein the flexible wire is partially positioned within the second groove such that the second groove guides linear movement of the flexible wire.

3. The rotatable wrist of claim 2, wherein a portion of the flexible wire extends from the first groove to the second groove and contacts the wrist capstan such that linear movement of the portion of the flexible wire that extends from the first groove to the second groove causes rotation of the wrist capstan.

4. The rotatable wrist of claim 2, wherein linear movement of the flexible wire through the first groove in a direction away from the rotatable wrist causes rotation of the rotatable wrist in a first rotational direction and causes linear movement of the flexible wire through the second groove in a direction towards the rotatable wrist, and
   wherein linear movement of the flexible wire through the second groove in the direction away from the rotatable wrist causes rotation of the rotatable wrist in a second rotational direction opposite the first rotational direction and causes linear movement of the flexible wire through the first groove in the direction towards the rotatable wrist.

5. The rotatable wrist of claim 4, wherein the wrist hub is non-rotatably coupled to a distal end of a positioning shaft, wherein the linear movement of the flexible wire through the first groove in a direction away from the rotatable wrist includes linear movement of a portion of the flexible wire extending from the first groove into the positioning shaft through the positioning shaft in a direction from the distal end of the positioning shaft towards a proximal end of the positioning shaft.

6. The rotatable wrist of claim 1, wherein the wrist capstan includes a grooved surface, and where the flexible wire includes a spherical terminal that contacts the grooved surface of the wrist capstan.

7. The rotatable wrist of claim 6, wherein the contact between the spherical terminal and the grooved surface of the wrist capstan increases the friction between the flexible wire and the wrist capstan during linear movement of the flexible wire.

8. The rotatable wrist of claim 1, further comprising a pivot joint connecting the wrist hub to a distal end of a positioning shaft, wherein the pivot joint is configured to controllably adjust an angle of the rotational axis of the rotatable wrist relative to a positioning shaft.

9. The rotatable wrist of claim 1, further comprising a universal joint connecting the wrist hub to a distal end of a positioning shaft, wherein the universal joint is configured to controllably adjust yaw and pitch angles of the rotational axis of the rotatable wrist.

10. The rotatable wrist of claim 1, wherein the wrist capstan is non-rotatably coupled to a gripper, wherein the wrist capstan further includes an actuation channel extending through a center of the wrist capstan, and wherein actuation of the gripper is controlled by at least one wire extending through the actuation channel.

11. The rotatable wrist of claim 1, further comprising a locking component for selectively attaching the rotatable wrist to a positioning shaft.

12. A rotatable wrist for placement and manipulation of an actuatable device, the rotatable wrist comprising:
   a wrist hub non-rotatably coupled to a distal end of a positioning shaft;
   a wrist capstan rotatably connected to the wrist hub and non-rotatably connected to the actuatable device; and
   a flexible wire loop extending through the wrist hub and partially contacting the wrist capstan, wherein linear movement of the flexible wire loop through the positioning shaft causes rotation of the wrist capstan due to friction between the flexible wire loop and the wrist capstan, wherein the wrist hub includes a first groove and a second groove, wherein the first groove is positioned at an angle relative to the positioning shaft, and wherein a first end of the flexible wire loop is positioned within the first groove such that the first groove guides linear movement of the first end of the flexible wire loop.

13. The rotatable wrist of claim 12, wherein the actuatable device includes a gripper.

14. The rotatable wrist of claim 12, wherein the positioning shaft is configured to control a position of the actuatable device in a cavity.

15. The rotatable wrist of claim 12, wherein the positioning shaft is configured to control a position of the actuatable device in a body cavity during minimally invasive surgical procedures.

16. The rotatable wrist of claim 12, wherein the wrist capstan includes a grooved surface, and wherein the flexible wire loop includes a spherical terminal that contacts the grooved surface of the wrist capstan providing friction between the flexible wire loop and the wrist capstan during linear movement of the flexible wire loop.

17. The rotatable wrist of claim 12, wherein the second groove is positioned at an angle relative to the positioning shaft, and wherein a second end of the flexible wire loop is positioned within the second groove such that the second groove guides linear movement of the second end of the flexible wire loop.

18. The rotatable wrist of claim 17, wherein a portion of the flexible wire loop extends from the first groove to the second groove and contacts the wrist capstan such that linear movement of the portion of the flexible wire loop that extends from the first groove to the second groove causes rotation of the wrist capstan.

19. The rotatable wrist of claim 12, further comprising an actuation channel extending through a center of the wrist capstan, wherein actuation of the actuatable device is controlled by at least one wire extending through the actuation channel.

20. The rotatable wrist of claim 12, further comprising a locking component for selectively attaching the rotatable wrist to the positioning shaft.

21. The rotatable wrist of claim 12, wherein the positioning shaft includes an actuatable continuum robot.

\* \* \* \* \*